US012415156B1

United States Patent
Fujiwara

(10) Patent No.: US 12,415,156 B1
(45) Date of Patent: Sep. 16, 2025

(54) THREE-WAY VALVE AND OXYGEN CONCENTRATOR

(71) Applicant: DAIKIN INDUSTRIES, LTD., Osaka (JP)

(72) Inventor: Takeshi Fujiwara, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 19/221,296

(22) Filed: May 28, 2025

Related U.S. Application Data

(63) Continuation of application No. PCT/JP2023/038636, filed on Oct. 26, 2023.

(30) Foreign Application Priority Data

Nov. 30, 2022 (JP) .................................. 2022-191721

(51) Int. Cl.
*B01D 53/04* (2006.01)
*A61M 16/10* (2006.01)
(Continued)

(52) U.S. Cl.
CPC ..... *B01D 53/0446* (2013.01); *B01D 53/0415* (2013.01); *F16K 11/22* (2013.01);
(Continued)

(58) Field of Classification Search
CPC ............ B01D 53/0446; B01D 53/0415; B01D 53/04; B01D 2256/12; B01D 2257/102;
(Continued)

(56) References Cited

U.S. PATENT DOCUMENTS

| | | | | |
|---|---|---|---|---|
| 5,827,358 A | * | 10/1998 | Kulish | B01D 53/0407 96/144 |
| 2007/0205384 A1 | * | 9/2007 | Kurosawa | F15B 13/0889 137/455 |

(Continued)

FOREIGN PATENT DOCUMENTS

JP 2020-168087 A 10/2020

OTHER PUBLICATIONS

International Search Report of corresponding PCT Application No. PCT/JP2023/038636 dated Jan. 23, 2024.
(Continued)

*Primary Examiner* — Frank M Lawrence, Jr.
(74) *Attorney, Agent, or Firm* — GLOBAL IP COUNSELORS, LLP

(57) ABSTRACT

A three-way valve includes a manifold, a valve body, and a switching mechanism. The manifold is provided with a flow path including first, second and third ports, first, second and third passages leading to the first, second and third ports, and a valve chamber that communicates with the first, second, and third passages. The valve body is accommodated in the valve chamber and is displaceable to a first position at which the first port and the third port communicate with each other or a second position at which the second port and the third port communicate with each other. The switching mechanism switches a position of the valve body to the first position or the second position. The manifold is configured by a plurality of manifold members that have a plate shape and are stacked in a plate thickness direction.

13 Claims, 18 Drawing Sheets

(51) Int. Cl.
 *F16K 11/048* (2006.01)
 *F16K 11/22* (2006.01)
 *F16K 31/365* (2006.01)

(52) U.S. Cl.
 CPC ........ *F16K 31/365* (2013.01); *B01D 2256/12* (2013.01); *B01D 2257/102* (2013.01); *B01D 2259/40003* (2013.01); *B01D 2259/402* (2013.01)

(58) Field of Classification Search
 CPC .... B01D 2259/40003; B01D 2259/402; F16K 11/22; F16K 31/365
 USPC ........... 95/96, 130, 138; 96/121; 128/205.24
 See application file for complete search history.

(56) References Cited

U.S. PATENT DOCUMENTS

2016/0312907 A1\* 10/2016 Mierendorf ......... F16K 27/0263
2024/0226797 A1\* 7/2024 Huang .................... F16K 11/22

OTHER PUBLICATIONS

International Preliminary Report of corresponding PCT Application No. PCT/JP2023/038636 dated Jun. 12, 2025.

\* cited by examiner

FIG. 17

| STEP | SUMMARY | ELECTROMAGNETIC VALVE A | | ELECTROMAGNETIC VALVE B | | PURGE VALVE |
| --- | --- | --- | --- | --- | --- | --- |
| | | 1→2 | 2→3 | 1→2 | 2→3 | 1↔2 |
| T1 | · HIGH-CONCENTRATION OXYGEN GAS IS SUPPLIED FROM SECOND ADSORPTION CYLINDER TO FIRST ADSORPTION CYLINDER | OPEN | CLOSED | OPEN | CLOSED | OPEN |
| T2 | · FIRST ADSORPTION CYLINDER IS PRESSURIZED<br>· SECOND ADSORPTION CYLINDER IS DECOMPRESSED | OPEN | CLOSED | CLOSED | OPEN | CLOSED |
| T3 | · HIGH-CONCENTRATION OXYGEN GAS IS SUPPLIED FROM FIRST ADSORPTION CYLINDER TO SECOND ADSORPTION CYLINDER | OPEN | CLOSED | CLOSED | OPEN | OPEN |
| T4 | · HIGH-CONCENTRATION OXYGEN GAS IS SUPPLIED FROM FIRST ADSORPTION CYLINDER TO SECOND ADSORPTION CYLINDER | OPEN | CLOSED | OPEN | CLOSED | OPEN |
| T5 | · SECOND ADSORPTION CYLINDER IS PRESSURIZED<br>· FIRST ADSORPTION CYLINDER IS DECOMPRESSED | CLOSED | OPEN | OPEN | CLOSED | CLOSED |
| T6 | · HIGH-CONCENTRATION OXYGEN GAS IS SUPPLIED FROM SECOND ADSORPTION CYLINDER TO FIRST ADSORPTION CYLINDER | CLOSED | OPEN | OPEN | CLOSED | OPEN |

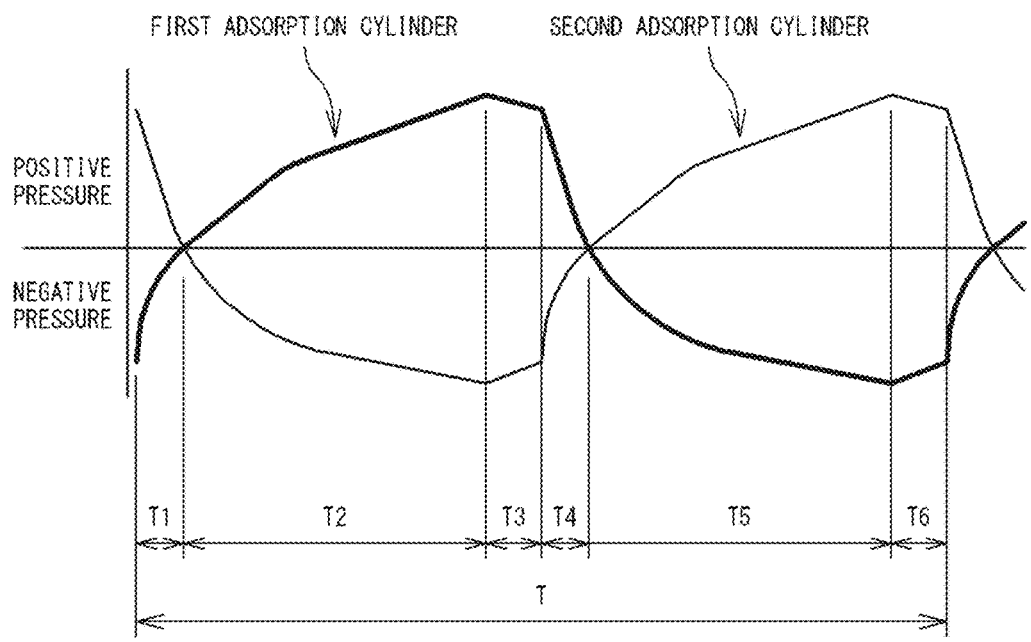

THREE-WAY VALVE AND OXYGEN CONCENTRATOR

CROSS-REFERENCE TO RELATED APPLICATIONS

This is a continuation of International Application No. PCT/JP2023/038636 filed on Oct. 26, 2023, which claims priority to Japanese Patent Application No. 2022-191721, filed on Nov. 30, 2022. The entire disclosures of these applications are incorporated by reference herein.

BACKGROUND

Technical Field

The present disclosure relates to a three-way valve and an oxygen concentrator including the three-way valve.

Background Art

There is known an oxygen concentrator that generates high concentration oxygen containing oxygen at a concentration higher than oxygen concentration in air and supplies the oxygen to a user. The oxygen concentrator is used, for example, when a patient (user) who has a disease in the lung and the function of the lung is deteriorated performs oxygen therapy.

In an oxygen concentrator in the related art, a three-way valve is used as a control valve that controls a pressurization and exhaust cycle of two adsorption cylinders. As a three-way valve used in an oxygen concentrator, for example, a three-way valve disclosed in Japanese Laid-Open Patent Publication No. 2020-168087 is known. The three-way valve disclosed in Japanese Laid-Open Patent Publication No. 2020-168087 is an internal pilot type three-way valve. The internal pilot type three-way valve includes a valve body including a coupling rod and a diaphragm, a manifold provided with a space that accommodates the valve body and a flow path of air inside, a pilot valve that switches an application destination of a pilot pressure, and the like, and is configured to move the valve body by the pilot pressure to switch the flow path that communicates with the two adsorption cylinders to a pressurization side and an exhaust side. The three-way valve disclosed in Japanese Laid-Open Patent Publication No. 2020-168087 is a double three-way valve having a structure in which two three-way valves are coupled and integrated (hereinafter, also referred to as an internal pilot type double three-way valve).

SUMMARY

A three-way valve of the present disclosure includes a manifold provided with a flow path including a first port, a first passage leading to the first port, a second port, a second passage leading to the second port, a third port, a third passage leading to the third port, and a valve chamber that communicates with the first passage, the second passage, and the third passage, a valve body that is accommodated in the valve chamber and is displaceable to a first position at which the first port and the third port communicate with each other or a second position at which the second port and the third port communicate with each other, and a switching mechanism that switches a position of the valve body to the first position or the second position, in which the manifold is configured by a plurality of manifold members that has a plate shape and is stacked in a plate thickness direction.

BRIEF DESCRIPTION OF THE DRAWINGS

FIG. 17 is a diagram for describing a relationship between a pressure change of one cycle of an adsorption cylinder and a switching state of a control valve of the oxygen concentrator.

DETAILED DESCRIPTION OF EMBODIMENT(S)

Hereinafter, an oxygen supply device of the present disclosure will be described in detail with reference to the accompanying drawings. The present disclosure should not be limited to the following exemplification, but is intended to include any modification recited in the claims within meanings and a scope equivalent to the scope of the claims.

(Overall Configuration of Three-Way Valve (Embodiment 1) of Present Disclosure)

Figure 1:
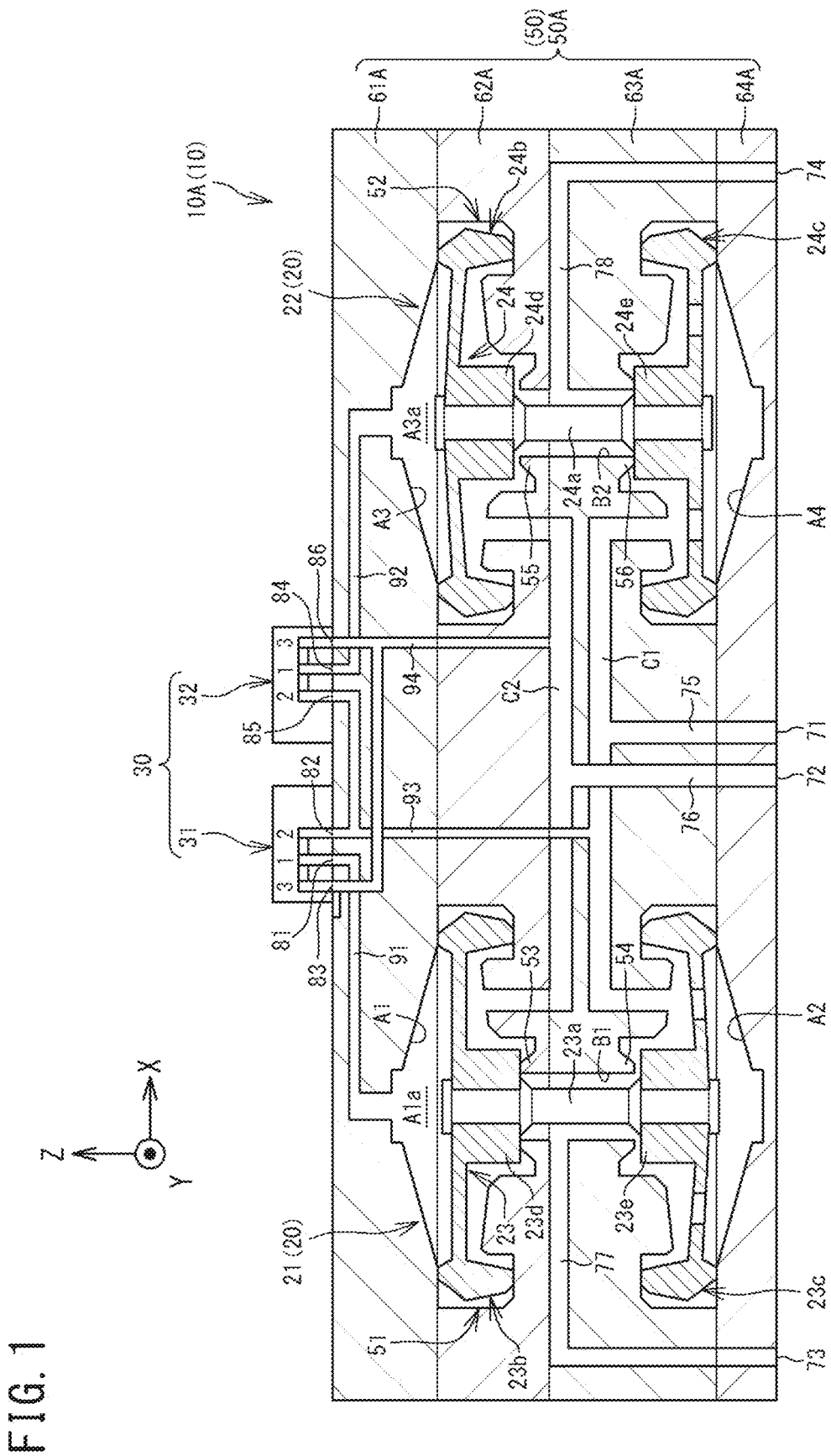
FIG. 1 is a schematic sectional view of a three-way valve (Embodiment 1) of the present disclosure.
Figure 2:
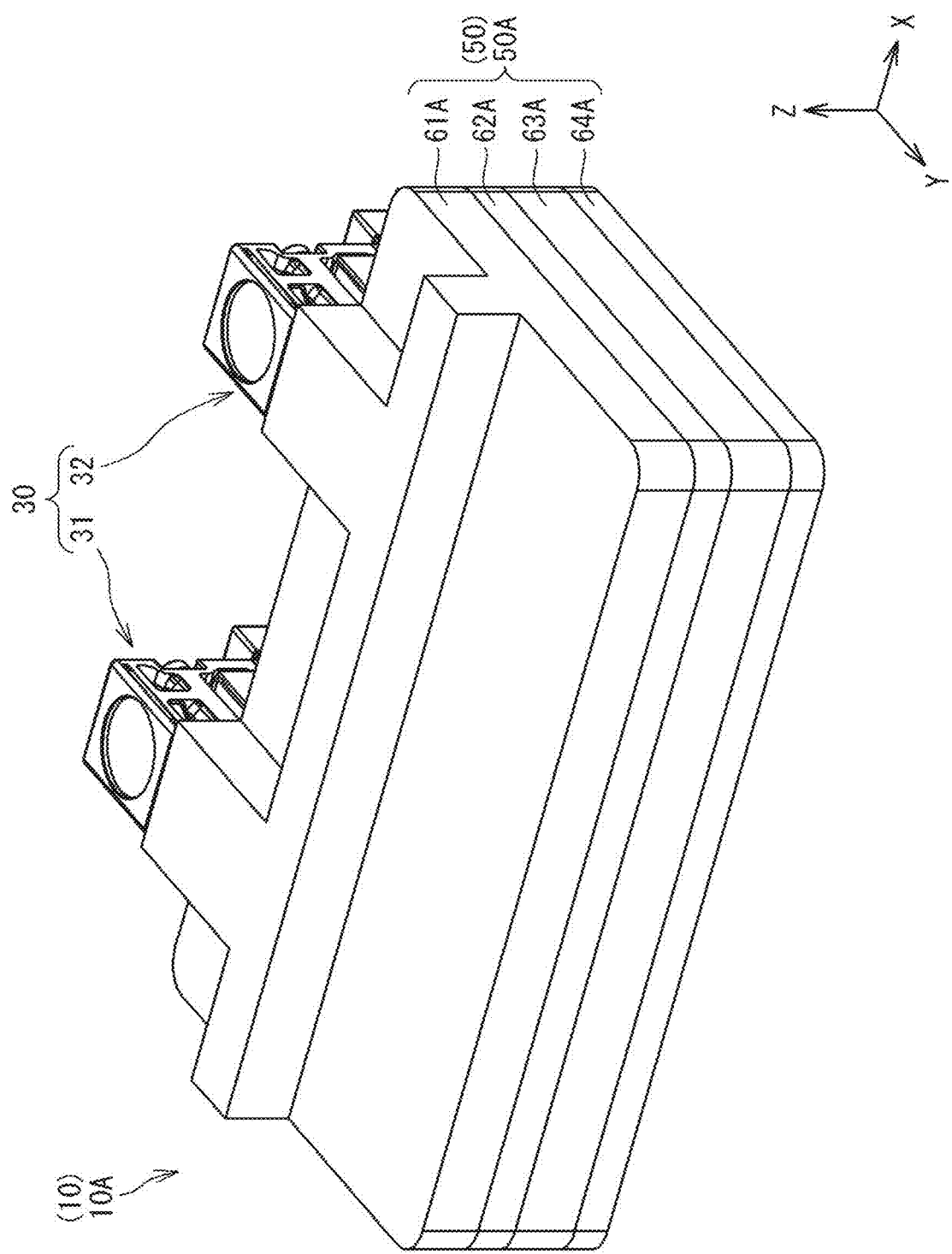
FIG. 2 is a schematic perspective view of the three-way valve (Embodiment 1) of the present disclosure.

FIG. 1 is a schematic sectional view of a three-way valve (Embodiment 1) of the present disclosure. FIG. 2 is a schematic perspective view of the three-way valve of the present disclosure. FIGS. 1 and 2 show a three-way valve 10 as an example of the three-way valve of the present disclosure. The three-way valve 10 shown in FIG. 1 is a three-way valve 10 according to Embodiment 1 of the present disclosure, and is also referred to as first three-way valve 10A in the following description. In the following description, when simply referred to as "three-way valve 10", a common configuration between the first three-way valve 10A according to Embodiment 1 and a three-way valve 10 according to Embodiment 2 (second three-way valve 10B described later) will be described.

The three-way valve 10 shown in FIGS. 1 and 2 is an internal pilot type double three-way valve. In the present embodiment, a three-way valve of the present disclosure will be described by exemplifying a three-way valve 10 which is an internal pilot type double three-way valve. In the present embodiment, the three-way valve 10 which is an internal pilot type double three-way valve will be described as an example. However, the three-way valve of the present disclosure may be a single (not double) three-way valve, and is not required to be a three-way valve activated by a pilot pressure.

As shown in FIGS. 1 and 2, the three-way valve 10 includes a control valve 20, a pilot mechanism 30, and a manifold 50. In the three-way valve 10 according to the present embodiment, the control valve 20 includes a first control valve 21 and a second control valve 22. In the three-way valve 10 according to the present embodiment, the pilot mechanism 30 includes a first pilot valve 31 and a second pilot valve 32. The manifold 50 includes a first valve chamber 51 that accommodates the first control valve 21 and a second valve chamber 52 that accommodates the second control valve 22. In such a manner, the three-way valve 10 shown in FIGS. 1 and 2 is a pilot type double three-way valve including a pair of the first control valve 21 and the second control valve 22, and a pair of the first pilot valve 31 and the second pilot valve 32. In the present embodiment, the three-way valve of the present disclosure will be described by exemplifying the three-way valve 10 which is a pilot type double three-way valve. In the following description, an X direction, a Y direction, and a Z direction are defined for the three-way valve 10 as follows. The X direction in this description is a direction including an arrangement direction of the first control valve 21 and the second control valve 22 and a direction parallel to the arrangement direction. The Z direction in this description is a direction including a displacement direction of each valve body (a first valve body 23 and a second valve body 24 described later) included in the first control valve 21 and the second control valve 22 and a direction parallel to the displacement direction. The Y direction is a direction perpendicular to the X direction and the Z direction. In the following description, in each drawing, a direction indicated by an arrow in the X direction is also referred to as a right side, an opposite direction to the direction is also referred to as a left side, a direction indicated by an arrow in the Y direction is also referred to as a front side, an opposite direction to the front side is also referred to as a rear side, a direction indicated by an arrow in the Z direction is also referred to as an upper side, and an opposite direction to the upper side is also referred to as a lower side.

(Control Valve)

As shown in FIGS. 1 and 2, the three-way valve 10 includes the first control valve 21 and the second control valve 22 arranged in a left-right direction (X direction).

The first control valve 21 includes the first valve body 23. The first valve body 23 includes a first coupling rod 23a, a first diaphragm 23b fixed to one end of the first coupling rod 23a, a second diaphragm 23c fixed to another end of the first coupling rod 23a, a first valve portion 23d provided closer to the first diaphragm 23b of the first coupling rod 23a, and a second valve portion 23e provided closer to the second diaphragm 23c of the first coupling rod 23a. The first valve body 23 is accommodated in the first valve chamber 51 of the manifold 50 in such an orientation that an axial direction of the first coupling rod 23a faces in the Z direction. The first diaphragm 23b defines a first chamber A1, and forms a pilot chamber A1a on one side (upper side in the present embodiment) across the first diaphragm 23b. The first diaphragm 23b is deformed in the first chamber A1 in response to a pressure of a pilot fluid supplied to the pilot chamber A1a. The first coupling rod 23a is displaced in the Z direction along with the deformation of the first diaphragm 23b. The second diaphragm 23c is deformed in a second chamber A2 along with the displacement of the first coupling rod 23a.

The second control valve 22 includes the second valve body 24. The second valve body 24 includes a second coupling rod 24a, a third diaphragm 24b fixed to one end of the second coupling rod 24a, a fourth diaphragm 24c fixed to another end of the second coupling rod 24a, a third valve portion 24d provided closer to the third diaphragm 24b of the second coupling rod 24a, and a fourth valve portion 24e provided closer to the fourth diaphragm 24c of the second coupling rod 24a. The second valve body 24 is accommodated in the second valve chamber 52 of the manifold 50 in such an orientation that an axial direction of the second coupling rod 24a faces in the Z direction. The third diaphragm 24b defines a third chamber A3, and forms a pilot chamber A3a on one side (upper side in the present embodiment) across the third diaphragm 24b. The third diaphragm 24b is deformed in the third chamber A3 in response to a pressure of a pilot fluid supplied to the pilot chamber A3a. The second coupling rod 24a is displaced in the Z direction along with the deformation of the third diaphragm 24b. The fourth diaphragm 24c is deformed in the fourth chamber A4 along with the deformation of the second coupling rod 24a.

(Pilot Valve)

The first pilot valve 31 is an electromagnetic valve that controls displacement (position switching) of the first valve body 23. The second pilot valve 32 is an electromagnetic valve that controls displacement (position switching) of the second valve body 24. Both of the first pilot valve 31 and the second pilot valve 32 according to the present embodiment are three-port valves. In FIG. 1 (the same applies to FIG. 8 described later), numbers "1", "2", or "3" assigned to near the first pilot valve 31 and the second pilot valve 32 represent port numbers of the valves.

(Manifold)

As shown in FIGS. 1 and 2, in the manifold 50, the first valve chamber 51 that accommodates the first valve body 23 includes the first chamber A1 that accommodates the first diaphragm 23*b*, the second chamber A2 that accommodates the second diaphragm 23*c*, and a first communication hole B1 that is a space that allows the first chamber A1 and the second chamber A2 to communicate with each other and accommodates the first coupling rod 23*a*. The manifold 50 includes, in the first valve chamber 51, the first valve seat 53 formed at an end of the first communication hole B1 closer to the first chamber A1 and a second valve seat 54 formed at an end of the first communication hole B1 closer to the second chamber A2. The first communication hole B1 is formed to have an axial direction parallel to the Z direction. In the first valve chamber 51, the first valve body 23 is configured to be displaceable in the Z direction.

The first valve seat 53 faces the first valve portion 23*d* of the first diaphragm 23*b* accommodated in the first chamber A1. In the first control valve 21, when the first valve portion 23*d* and the first valve seat 53 are apart from each other, the fluid can flow between the first chamber A1 (a portion on another side (lower side) across the first diaphragm 23*b*) and the first communication hole B1, and when the first valve portion 23*d* and the first valve seat 53 are in close contact with each other, the fluid cannot flow between the first chamber A1 and the first communication hole B1. The second valve seat 54 faces the second valve portion 23*e* of the second diaphragm 23*c* accommodated in the second chamber A2. In the first control valve 21, the fluid can flow between the second chamber A2 and the first communication hole B1 when the second valve portion 23*e* and the second valve seat 54 are apart from each other, and the fluid cannot flow between the second chamber A2 and the first communication hole B1 when the second valve portion 23*e* and the second valve seat 54 are in close contact.

Among the positions of the first control valve 21, a position where the first valve portion 23*d* and the first valve seat 53 are in close contact with each other and the second valve portion 23*e* and the second valve seat 54 are apart from each other is referred to as a first position P1, and a position where the first valve portion 23*d* and the first valve seat 53 are apart from each other and the second valve portion 23*e* and the second valve seat 54 are in close contact with each other is referred to as a second position P2.

In the manifold 50, the second valve chamber 52 accommodating the second valve body 24 includes the third chamber A3 accommodating the third diaphragm 24*b*, the fourth chamber A4 accommodating the fourth diaphragm 24*c*, and the second communication hole B2 that is a space that allows the third chamber A3 the fourth chamber A4 to communicate with each other and accommodating the second coupling rod 24*a*. The manifold 50 includes a third valve seat 55 formed at an end of the second communication hole B2 closer to the third chamber A3 and a fourth valve seat 56 formed at an end of the second communication hole B2 closer to the fourth chamber A4 in the second valve chamber 52. The second communication hole B2 is formed to have an axial direction parallel to the Z direction. In the second valve chamber 52, the second valve body 24 is configured to be displaceable in the Z direction.

The third valve seat 55 faces the third valve portion 24*d* of the third diaphragm 24*b* accommodated in the third chamber A3. In the second control valve 22, when the third valve portion 24*d* and the third valve seat 55 are apart from each other, the fluid can flow between the third chamber A3 (a portion on another side (lower side) across the third diaphragm 24*b*) and the second communication hole B2, and when the third valve portion 24*d* and the third valve seat 55 are in close contact with each other, the fluid cannot flow between the third chamber A3 and the second communication hole B2. The fourth valve seat 56 faces the fourth valve portion 24*e* of the fourth diaphragm 24*c* accommodated in the fourth chamber A4. In the second control valve 22, when the fourth valve portion 24*e* and the fourth valve seat 56 are apart from each other, the fluid can flow between the fourth chamber A4 and the second communication hole B2, and when the fourth valve portion 24*e* and the fourth valve seat 56 are in close contact with each other, the fluid cannot flow between the fourth chamber A4 and the second communication hole B2.

Among the positions of the second control valve 22, a position where the third valve portion 24*d* and the third valve seat 55 are in close contact with each other and the fourth valve portion 24*e* and the fourth valve seat 56 are apart from each other is referred to as a first position P1, and a position where the third valve portion 24*d* and the third valve seat 55 are apart from each other and the fourth valve portion 24*e* and the fourth valve seat 56 are in close contact with each other is referred to as a second position P2. In other words, in the first control valve 21 and the second control valve 22, a position when the first valve body 23 and the second valve body 24 are displaced to an uppermost side is referred to as the second position P2, and a position when the first valve body 23 and the second valve body 24 are displaced to a lowermost side is referred to as the first position P1.

In the manifold 50, a second connecting passage C2 that allows the first chamber A1 and the third chamber A3 to communicate with each other and a first connecting passage C1 that allows the second chamber A2 and the fourth chamber A4 to communicate with each other are formed inside.

The manifold 50 includes an air supply port 71, an exhaust port 72, a first air supply/exhaust port 73, and a second air supply/exhaust port 74 on an outer surface of the manifold 50. The three-way valve 10 of the present disclosure switches the positions of the first valve body 23 of the first control valve 21 and the second valve body 24 of the second control valve 22 to allow one of the first air supply/ exhaust port 73 or the second air supply/exhaust port 74 to communicate with the air supply port 71 while allowing another of the first air supply/exhaust port 73 and the second air supply/exhaust port 74 to communicate with the exhaust port 72. In the three-way valve 10 according to the present embodiment, the air supply port 71 and the exhaust port 72 are shared by the first control valve 21 and the second control valve 22. However, the first control valve 21 may have a dedicated air supply port and a dedicated exhaust port, and the second control valve 22 may have a dedicated air supply port and a dedicated exhaust port.

The manifold 50 includes an air supply passage 75 that allows the air supply port 71 and the first connecting passage C1 to communicate with each other, an exhaust passage 76 that allows the exhaust port 72 and the second connecting passage C2 to communicate with each other, a first air supply/exhaust passage 77 that allows the first air supply/ exhaust port 73 and the first valve chamber 51 to communicate with each other, and a second air supply/exhaust passage 78 that allows the second air supply/exhaust port 74 and the second valve chamber 52 to communicate with each other.

The manifold 50 includes, on the outer surface, a first pilot port 81, a second pilot port 82, and a third pilot port 83 to which the first pilot valve 31 is connected, and a fourth pilot port 84, a fifth pilot port 85, and a sixth pilot port 86 to which the second pilot valve 32 is connected. The manifold 50 includes a first pilot passage 91 that allows the first pilot port 81 and the first valve chamber 51 to communicate with each other, a second pilot passage 92 that allows the fourth pilot port 84 and the second valve chamber 52 to communicate with each other, a third pilot passage 93 that allows the second pilot port 82 and the fifth pilot port 85 to communicate with the first connecting passage C1, and a fourth pilot passage 94 that allows the third pilot port 83 and the sixth pilot port 86 to communicate with the second connecting passage C2.

As shown in FIG. 1, the first pilot valve 31 and the second pilot valve 32 are three-port valves. The first pilot valve 31 is attached to a rear surface of the manifold 50 such that the first pilot passage 91 is connected to the first port "1", the third pilot passage 93 is connected to the second port "2", and the fourth pilot passage 94 is connected to the third port "3". The second pilot valve 32 is attached to the rear surface of the manifold 50 such that the second pilot passage 92 is connected to the first port "1", the third pilot passage 93 is connected to the second port "2", and the fourth pilot passage 94 is connected to the third port "3".

(Manifold of Three-Way Valve According to Embodiment 1)

Figure 3A:
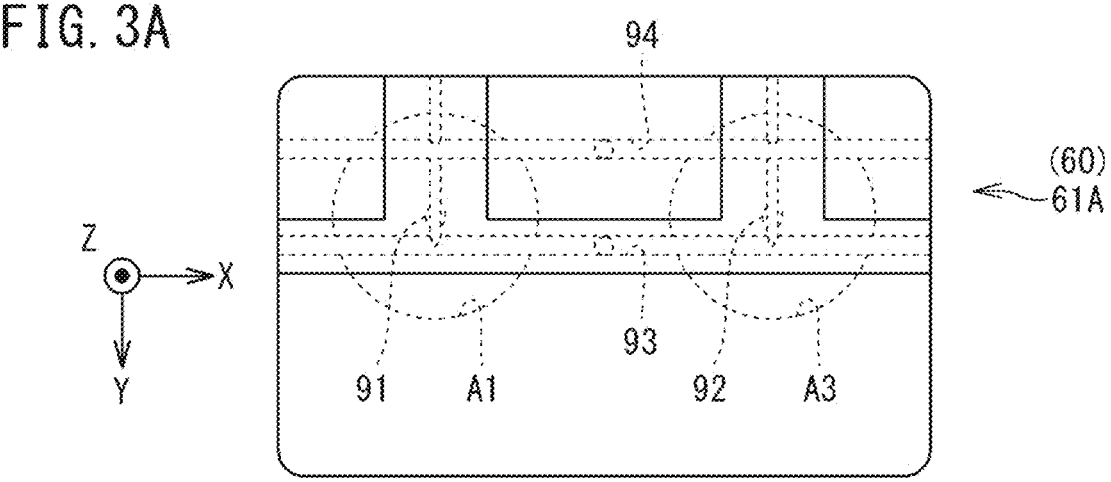
FIG. 3A is a top view of a first manifold member in a first three-way valve.
Figure 3B:
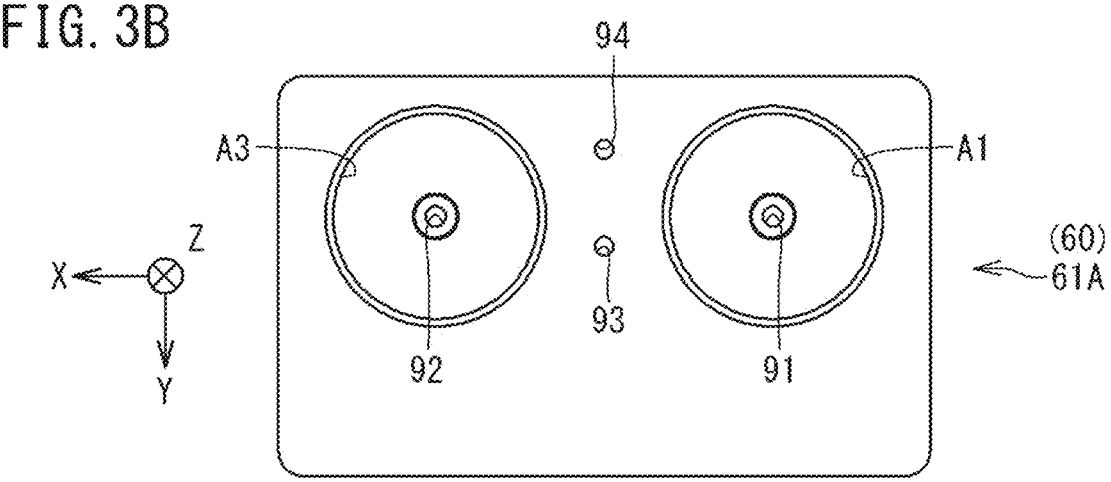
FIG. 3B is a bottom view of the first manifold member in the first three-way valve.
Figure 3C:
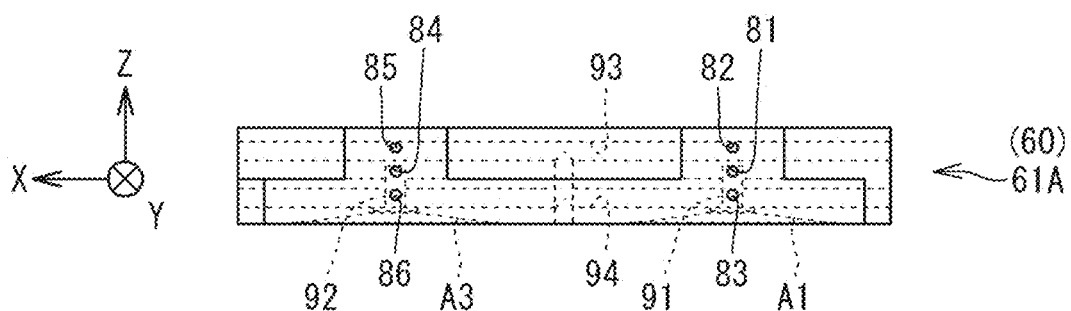
FIG. 3C is a rear view of the first manifold member in the first three-way valve.
Figure 4A:
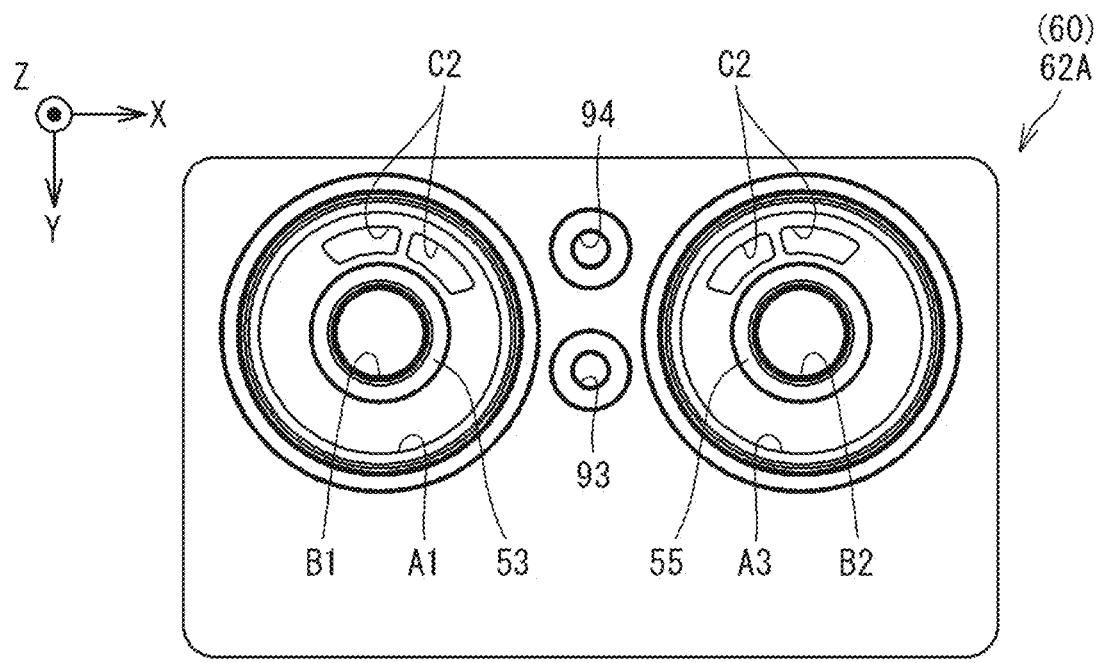
FIG. 4A is a top view of a second manifold member in the first three-way valve.
Figure 4B:
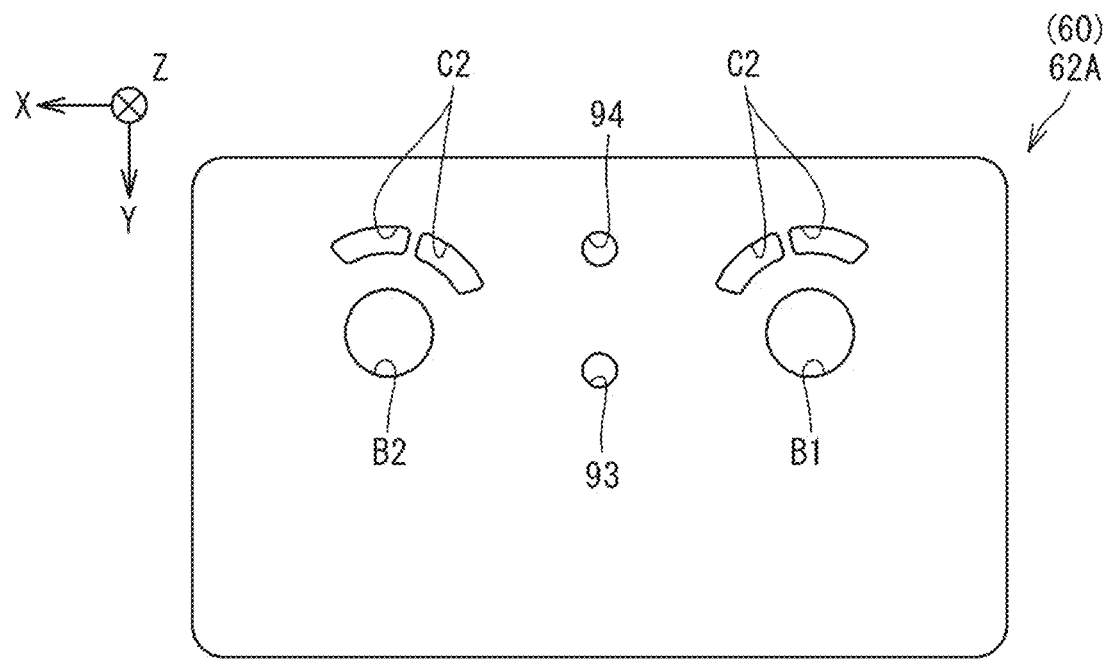
FIG. 4B is a bottom view of the second manifold member in the first three-way valve.
Figure 5A:
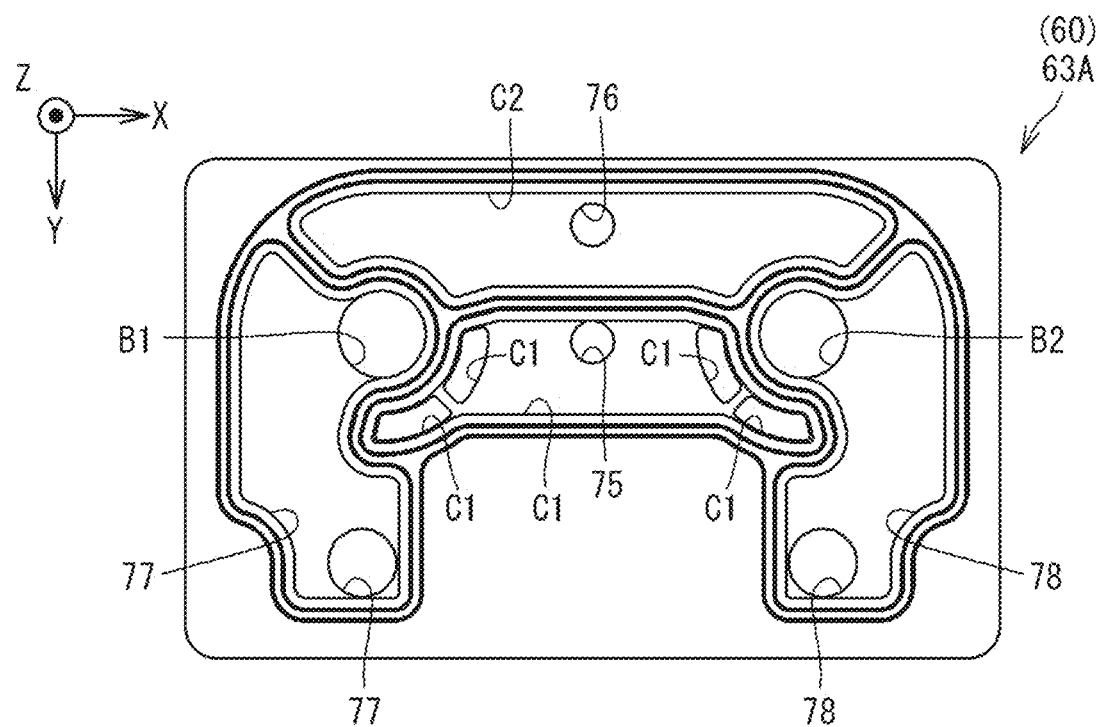
FIG. 5A is a top view of a third manifold member in the first three-way valve.
Figure 5B:
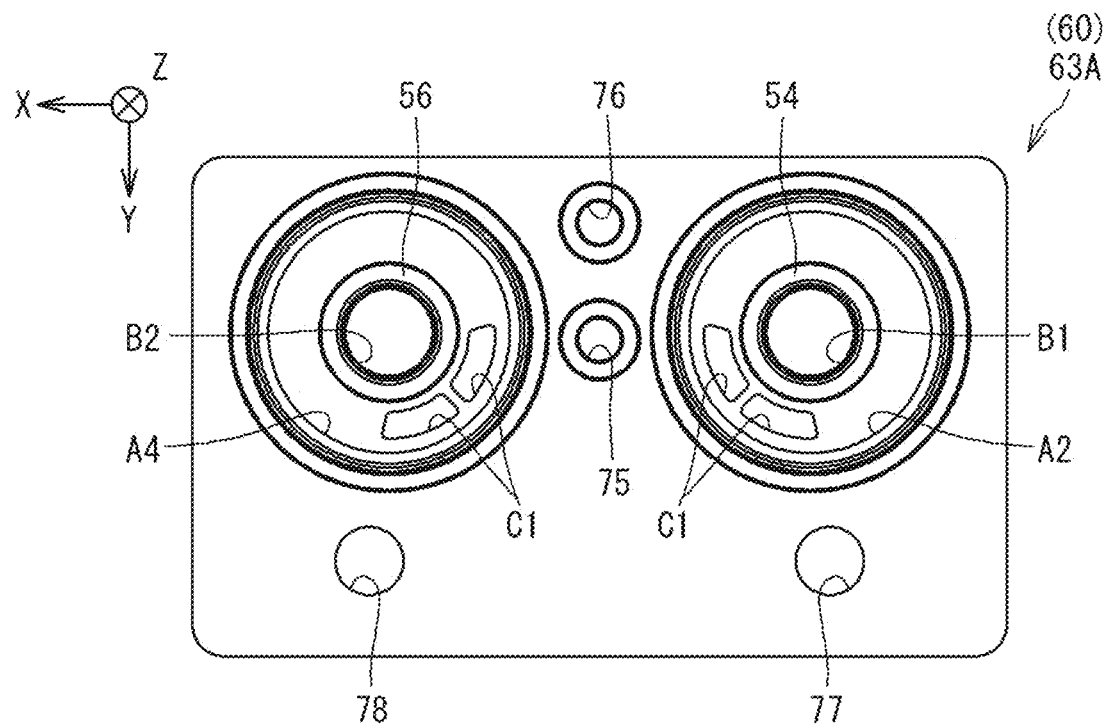
FIG. 5B is a bottom view of the third manifold member in the first three-way valve.
Figure 6A:
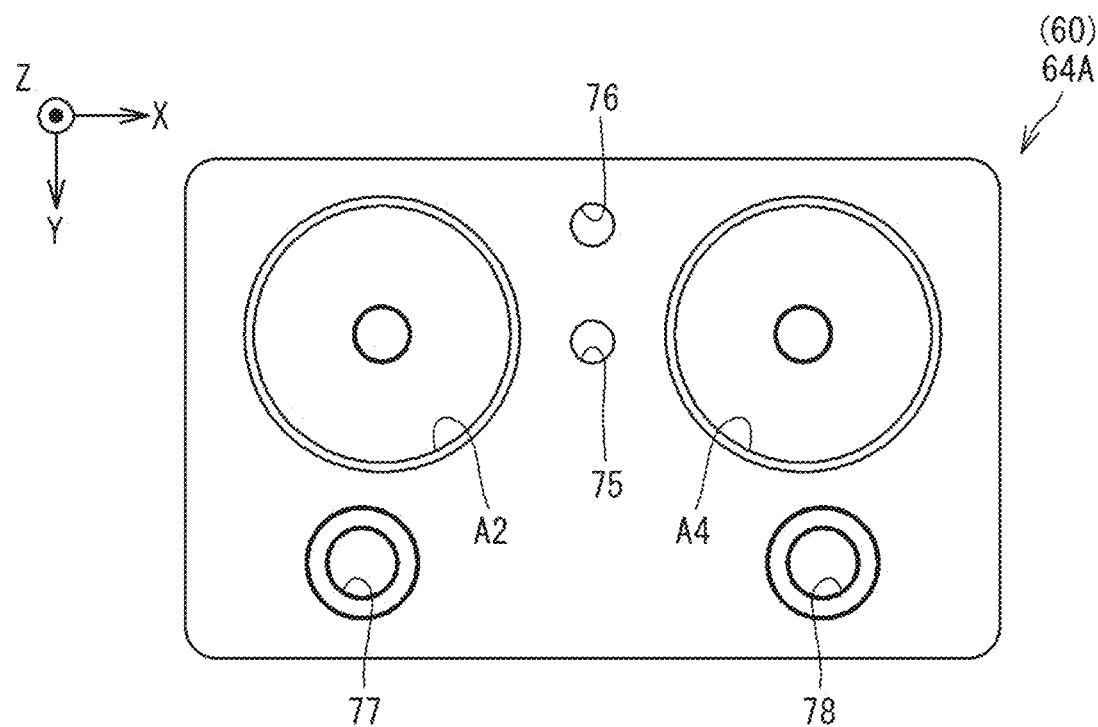
FIG. 6A is a top view of a fourth manifold member in the first three-way valve.
Figure 6B:
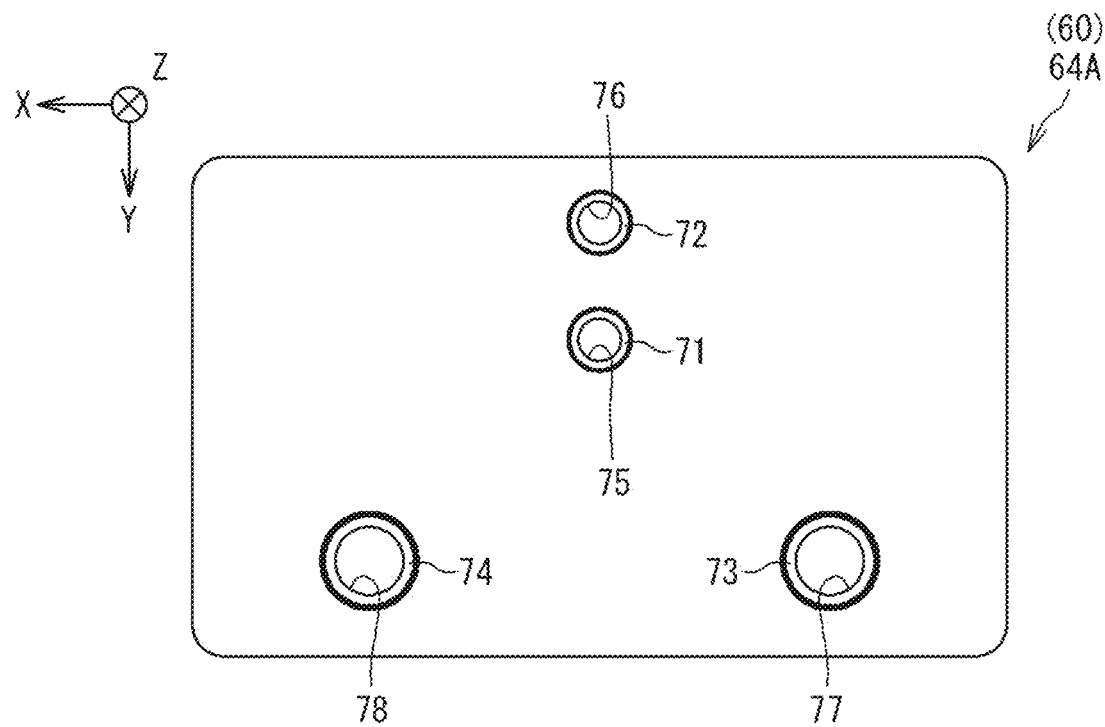
FIG. 6B is a bottom view of the fourth manifold member in the first three-way valve.

FIG. 3A is a top view of a first manifold member in the first three-way valve. FIG. 3B is a bottom view of the first manifold member in the first three-way valve. FIG. 3C is a rear view of the first manifold member in the first three-way valve. FIG. 4A is a top view of a second manifold member in the first three-way valve. FIG. 4B is a bottom view of the second manifold member in the first three-way valve. FIG. 5A is a top view of a third manifold member in the first three-way valve. FIG. 5B is a bottom view of the third manifold member in the first three-way valve. FIG. 6A is a top view of a fourth manifold member in the first three-way valve. FIG. 6B is a bottom view of the fourth manifold member in the first three-way valve. As shown in FIGS. 1 and 2, the manifold 50 constituting the first three-way valve 10A includes four plate-shaped manifold members 60. In the following description, the manifold 50 in the first three-way valve 10A is also referred to as a first manifold 50A.

The first manifold 50 includes a first manifold member 60 (hereinafter, referred to as a first manifold member 61A), a second manifold member 60 (hereinafter, referred to as a second manifold member 62A), a third manifold member 60 (hereinafter, referred to as a third manifold member 63A), and a fourth manifold member 60 (hereinafter, referred to as a fourth manifold member 64A).

The first manifold 50A is configured by stacking the first manifold member 61A, the second manifold member 62A, the third manifold member 63A, and the fourth manifold member 64A in a plate thickness direction in order from the upper side in the axial direction (Z direction) of the first coupling rod 23a accommodated in the first valve chamber 51 and the second coupling rod 24a accommodated in the second valve chamber 52.

As shown in FIGS. 1, 3A, and 3B, the first manifold member 61A is provided with a part of the first chamber A1, a part of the third chamber A3, the first pilot port 81, the second pilot port 82, the third pilot port 83, the fourth pilot port 84, the fifth pilot port 85, the sixth pilot port 86, the first pilot passage 91, the second pilot passage 92, a part of the third pilot passage 93, and a part of the fourth pilot passage 94.

As shown in FIGS. 1, 4A, and 4B, the second manifold member 62A is provided with a part of the first chamber A1, a part of the third chamber A3, a part of the first communication hole B1, a part of the second communication hole B2, a part of the first connecting passage C1, a part of the second connecting passage C2, the first valve seat 53, the third valve seat 55, a part of the first air supply/exhaust passage 77, a part of the second air supply/exhaust passage 78, a part of the third pilot passage 93, and a part of the fourth pilot passage 94.

In the first manifold 50A, the first chamber A1 and the third chamber A3 are formed across two manifold members 60, and include the first manifold member 61A and the second manifold member 62A.

As shown in FIGS. 1, 5A, and 5B, the third manifold member 63A is provided with a part of the second chamber A2, a part of the fourth chamber A4, a part of the first communication hole B1, a part of the second communication hole B2, a part of the first connecting passage C1, a part of the second connecting passage C2, the second valve seat 54, the fourth valve seat 56, a part of the air supply passage 75, a part of the exhaust passage 76, a part of the first air supply/exhaust passage 77, a part of the second air supply/exhaust passage 78, a part of the third pilot passage 93, and a part of the fourth pilot passage 94.

In the first manifold 50A, the first connecting passage C1 and the second connecting passage C2 are configured by recesses formed in a boundary surface between the second manifold member 62A and the third manifold member 63A. Specifically, the first connecting passage C1 and the second connecting passage C2 are configured by a space surrounded by a plane formed on a lower surface (boundary surface) of the second manifold member 62A and a recess formed on an upper surface (boundary surface) of the third manifold member 63A. The first connecting passage C1 and the second connecting passage C2 may be configured by a space surrounded by a recess formed in the lower surface (boundary surface) of the second manifold member 62A and a plane formed in the upper surface (boundary surface) of the third manifold member 63A, or may be configured by a space surrounded by a recess formed in the lower surface (boundary surface) of the second manifold member 62A and a recess formed in the upper surface (boundary surface) of the third manifold member 63A. The "boundary surface" between the adjacent manifold members 60 here includes a mating surface where the manifold members 60 are in contact with each other and a virtual surface obtained by extending the mating surface to a portion (space) where the recess exists.

In other words, in the first manifold 50A, the first connecting passage C1 and the second connecting passage C2 are formed in a range including the boundary surface between the adjacent manifold members 60 (the second manifold member 62A and the third manifold member 63A). In the present embodiment, a case where both the first connecting passage C1 and the second connecting passage C2 are formed in the range including the boundary surface between the adjacent manifold members 60 is exemplified. However, the first manifold 50A of the present disclosure may have a configuration in which one of the first connecting passage C1 or the second connecting passage C2 is drilled in the manifold member 60.

For example, in a case where the manifold has one metal lump (block) as in the related art, passages such as the first connecting passage C1 and the second connecting passage C2 are drilled in the block by using a drill or the like. Since such a passage formed by a drill or the like has a circular sectional shape, a margin other than the passage has to be large, and as a result, the block is increased in size and weight. On the other hand, as in the manifold 50 of the present disclosure, when the plate-shaped manifold members 60 are stacked in the plate thickness direction, passages such as the first connecting passage C1 and the second connecting passage C2 can be formed by recesses provided in the range including the boundary surface between the adjacent manifold members 60. In the manifold 50 of the present disclosure, the passage extending in a direction orthogonal to a stacking direction of the manifold members 60 can be expanded in the front-rear direction and the left-right direction, and a degree of freedom of the sectional shape of such a passage is higher than in the related art. In the manifold 50 having such a configuration, a margin other than the passages can be suppressed, and as a result, the manifold can be reduced in size and weight.

As shown in FIGS. 1, 6A, and 6B, the fourth manifold member 64A is provided with a part of the second chamber A2, a part of the fourth chamber A4, the air supply port 71, a part of the air supply passage 75, the exhaust port 72, a part of the exhaust passage 76, the first air supply/exhaust port 73, a part of the first air supply/exhaust passage 77, the second air supply/exhaust port 74, and a part of the second air supply/exhaust passage 78.

In the first manifold 50A, the second chamber A2 and the fourth chamber A4 are formed across two manifold members 60, and include the third manifold member 63A and the fourth manifold member 64A.

In the first manifold 50A, the first communication hole B1 and the second communication hole B2 are formed to have axial directions parallel to the stacking direction of the manifold members 60. In the first manifold 50A, the first communication hole B1 and the second communication hole B2 are formed across two manifold members 60 (the second manifold member 62A and the third manifold member 63A).

(Operation of Three-Way Valve)

Figure 7A:
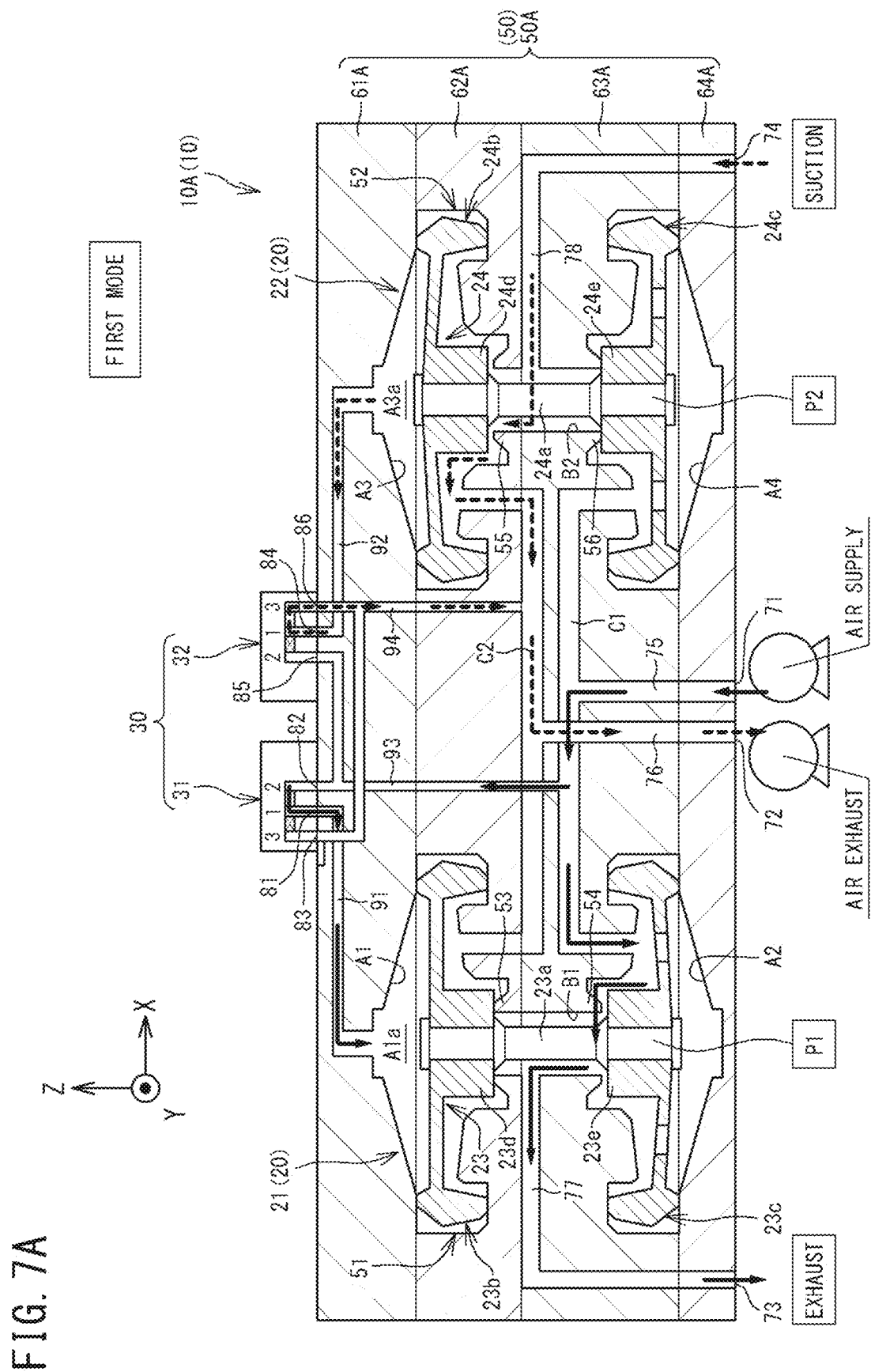
FIG. 7A is an explanatory diagram of an operation (first mode) of the three-way valve of the present disclosure.
Figure 7B:
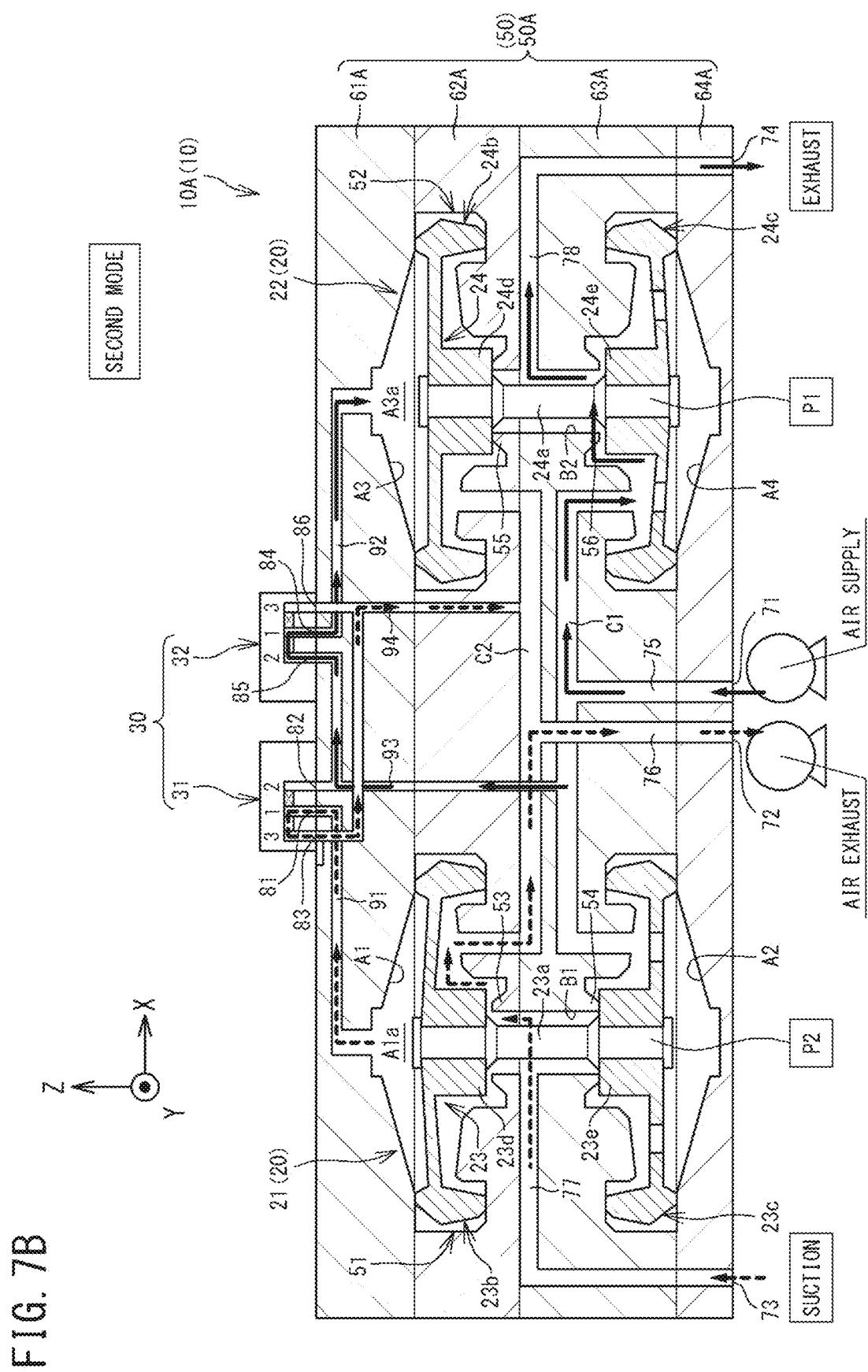
FIG. 7B is an explanatory diagram of an operation (second mode) of the three-way valve of the present disclosure.

FIG. 7B is an explanatory diagram of an operation of the three-way valve of the present disclosure. As shown in FIG. 7, the three-way valve 10 of the present disclosure is used in a form in which compressed air is supplied to the air supply port 71 and gas is sucked and exhausted from the exhaust port 72. The three-way valve 10 having such a configuration includes a pair of adsorption cylinders, and is suitable for use in an oxygen concentrator of a vacuum pressure swing adsorption system (VPSA) that sucks and decompresses one adsorption cylinder while compressed air is supplied to the other adsorption cylinder. Although the three-way valve 10 shown in the present embodiment exemplifies a case where air is sucked and exhausted from the exhaust port 72, the three-way valve 10 of the present disclosure may exhaust air from the exhaust port 72 by opening the exhaust port 72 to atmosphere without sucking air. The three-way valve 10 in this case includes a pair of adsorption cylinders, and is suitable for use in an oxygen concentrator of a pressure swing adsorption system (PSA) in which while compressed air is supplied to one of the adsorption cylinders, the other adsorption cylinder is opened to the atmosphere to be decompressed.

In a first mode, the three-way valve 10 switches the "1" port and the "2" port of the first pilot valve 31 to communicate with each other, and switches the "1" port and the "3" port of the second pilot valve 32 to communicate with each other.

At this time, in the first control valve 21, the pilot chamber A1a communicates with the air supply passage 75 via the first pilot passage 91, the first pilot valve 31, the third pilot passage 93, and the first connecting passage C1. As a result, the compressed air is supplied to the pilot chamber A1a (a positive pilot pressure is applied).

In the first control valve 21, when the compressed air is supplied to the pilot chamber A1a, a pilot pressure is applied to the first diaphragm 23b, and the first coupling rod 23a is thus displaced from the first chamber A1 toward the second chamber A2. At this time, the first valve portion 23d is pressed against the first valve seat 53, and a flow of air from the first communication hole B1 to the first chamber A1 (a portion below the first diaphragm 23b) is sealed. In this description, the position of the first valve body 23 at this time is referred to as a first position P1.

Furthermore, in the first control valve 21, at this time, the second valve portion 23e is apart from the second valve seat 54, and the first connecting passage C1 and the first air supply/exhaust passage 77 thus communicate with each other via the first communication hole B1 and the second chamber A2. As a result, air is supplied from the air supply passage 75 to the first air supply/exhaust passage 77 via the first control valve 21.

At this time, in the second control valve 22, the pilot chamber A3a communicates with the exhaust passage 76 via the second pilot passage 92, the second pilot valve 32, the fourth pilot passage 94, and the second connecting passage C2. As a result, air is sucked and exhausted from the pilot chamber A3a (negative pilot pressure is applied).

In the second control valve 22, when air is sucked and exhausted from the pilot chamber A3a, a negative pilot pressure is applied to the third diaphragm 24b, and the second coupling rod 24a is thus displaced from the fourth chamber A4 toward the third chamber A3. At this time, the fourth valve portion 24e is pressed against the fourth valve seat 56, and a flow of air from the fourth chamber A4 to the second communication hole B2 is sealed.

Furthermore, in the second control valve 22, at this time, the third valve portion 24d is apart from the third valve seat 55, and the second connecting passage C2 and the second air supply/exhaust passage 78 thus communicate with each other via the second communication hole B2 and the third chamber A3 (a portion below the third diaphragm 24b). As a result, gas is exhausted from the exhaust passage 76 to the second air supply/exhaust passage 78 via the second control valve 22. In this description, the position of the second valve body 24 at this time is referred to as a second position P1.

Furthermore, in the second control valve 22, the pilot chamber A3a communicates with the exhaust passage 76 via the second pilot passage 92, the second pilot valve 32, the fourth pilot passage 94, and the second connecting passage C2. In the second control valve 22, air is sucked and exhausted from the pilot chamber A3a, and a negative pilot pressure is thus applied to the second valve body 24 (third diaphragm 24b).

In the second control valve 22, when air is sucked and exhausted from the pilot chamber A3a, a negative pilot pressure is applied to the third diaphragm 24b, and the second valve body 24 (second coupling rod 24a) is thus reliably displaced from the first position P1 to the second position P2. Therefore, the second control valve 22 can ensure reliability of the operation.

In such a manner, in the first mode, the three-way valve 10 of the present disclosure switches the flow of the fluid so as to allow a flow of supply air from the air supply port 71 toward the first air supply/exhaust port 73 to exhaust the gas from the first air supply/exhaust port 73, and to allow a flow of exhaust air from the second air supply/exhaust port 74 toward the exhaust port 72 to suck the gas from the second air supply/exhaust port 74.

In a second mode, the three-way valve 10 of the present disclosure switches the "1" port and the "3" port of the first pilot valve 31 to communicate with each other, and switches the "1" port and the "2" port of the second pilot valve 32 to communicate with each other.

At this time, in the first control valve 21, the pilot chamber A1a communicates with the exhaust passage 76 via the first pilot passage 91, the first pilot valve 31, the fourth pilot passage 94, and the second connecting passage C2. As a result, air is sucked and exhausted from the pilot chamber A1a (negative pilot pressure is applied).

In the first control valve 21, air is sucked and exhausted from the pilot chamber A1a of the first chamber A1, a negative pilot pressure is applied to the first diaphragm 23b, and the first coupling rod 23a is thus displaced from the second chamber A2 in the Z direction toward the first chamber A1. At this time, the second valve portion 23e is pressed against the second valve seat 54, and a flow of air from the second chamber A2 to the first communication hole B1 is sealed.

Furthermore, in the first control valve 21, at this time, the first valve portion 23d is apart from the first valve seat 53, and the second connecting passage C2 and the first air supply/exhaust passage 77 thus communicate with each other via the first communication hole B1 and the first chamber A1 (a portion below the first diaphragm 23b). As a result, gas is exhausted from the exhaust passage 76 to the first air supply/exhaust passage 77 via the first control valve 21. In this description, the position of the first valve body 23 at this time is referred to as a second position P1.

Furthermore, in the first control valve 21, the pilot chamber A1a communicates with the exhaust passage 76 via the first pilot passage 91, the first pilot valve 31, the fourth pilot passage 94, and the second connecting passage C2. In the first control valve 21, air is sucked and exhausted from the pilot chamber A1a, and a negative pilot pressure is thus applied to the first valve body 23 (first diaphragm 23b).

In the first control valve 21, when air is sucked and exhausted from the pilot chamber A1a, a negative pilot pressure is applied to the first diaphragm 23b, and the first valve body 23 (first coupling rod 23a) is thus reliably displaced from the first position P1 to the second position P2. Therefore, the first control valve 21 can ensure the reliability of the operation.

At this time, in the second control valve 22, the pilot chamber A3a communicates with the air supply passage 75 via the second pilot passage 92, the second pilot valve 32, the third pilot passage 93, and the first connecting passage C1. As a result, the compressed air is supplied to the pilot chamber A3a (a positive pilot pressure is applied).

In the second control valve 22, when the compressed air is supplied to the pilot chamber A3a, a positive pilot pressure is applied to the third diaphragm 24b, and the second coupling rod 24a is thus displaced from the third chamber A3 toward the fourth chamber A4 in the Z direction. At this time, the third valve portion 24d is pressed against the third valve seat 55, and a flow of air from the third chamber A3 (a portion below the third diaphragm 24b) to the second communication hole B2 is sealed. In this description, the position of the second valve body 24 at this time is referred to as a first position P1.

Furthermore, in the second control valve 22, at this time, the fourth valve portion 24e is apart from the fourth valve seat 56, and the first connecting passage C1 and the second air supply/exhaust passage 78 thus communicate with each other via the second communication hole B2 and the fourth chamber A4. As a result, air is supplied from the air supply passage 75 to the second air supply/exhaust passage 78 via the second control valve 22.

In such a manner, in the second mode, the three-way valve 10 of the present disclosure switches the flow of the fluid so as to allow a flow of the supply air from the air supply port 71 toward the second air supply/exhaust port 74 to exhaust the gas from the second air supply/exhaust port 74, and to allow a flow of the exhaust air from the first air supply/exhaust port 73 toward the exhaust port 72 to suck the gas from the first air supply/exhaust port 73.

In the three-way valve 10 of the present disclosure, by alternately switching between the first mode and the second mode, the first air supply/exhaust port 73 can be alternately used as an air supply port and an exhaust port, and the second air supply/exhaust port 74 can be alternately used as a port on a side different from the first air supply/exhaust port out of the air supply port and the exhaust port.

{Three-Way Valve According to Embodiment 2)

Figure 8:
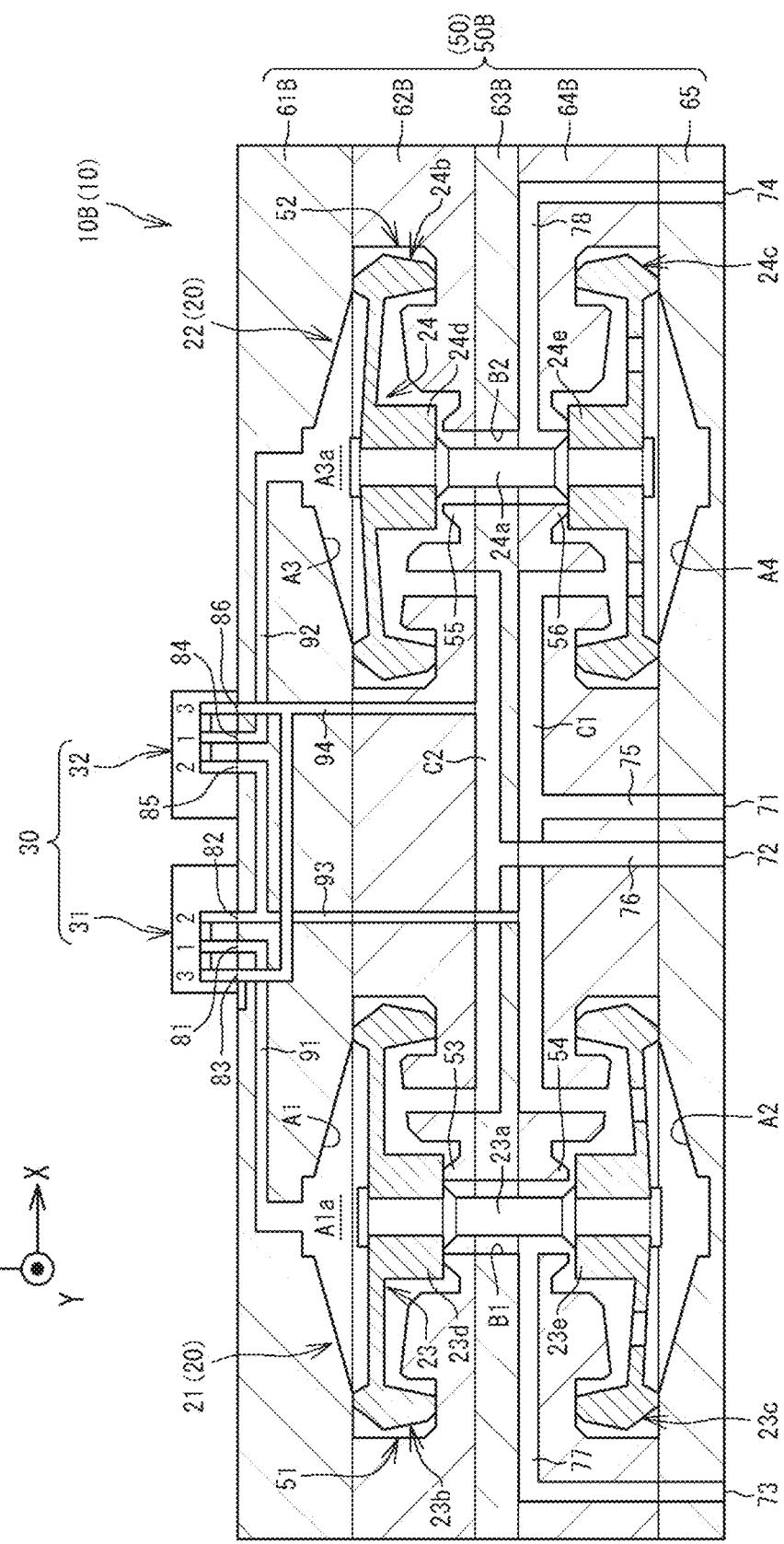
FIG. 8 is a schematic sectional view of a three-way valve (Embodiment 2) of the present disclosure.
Figure 9:
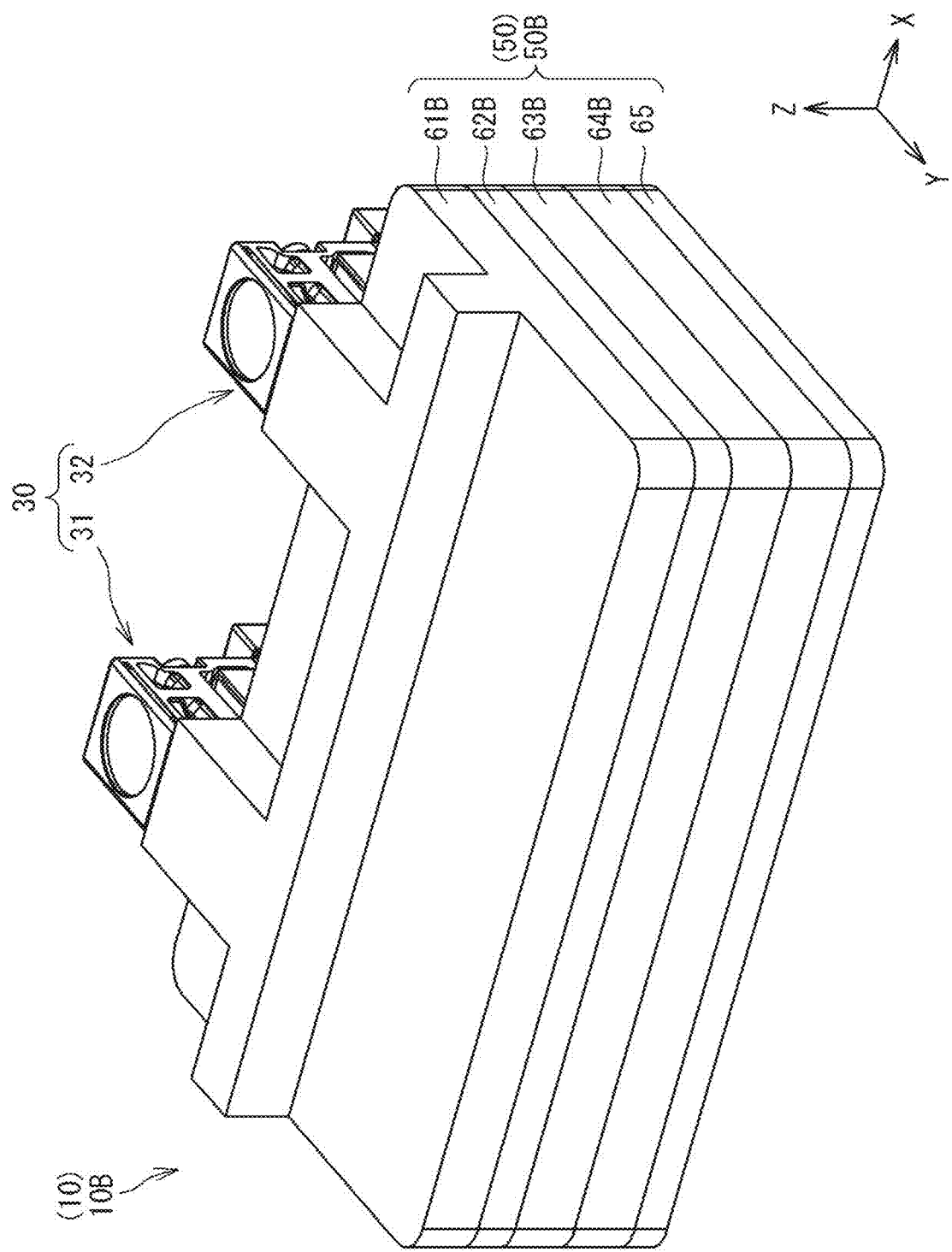
FIG. 9 is a schematic perspective view of the three-way valve (Embodiment 2) of the present disclosure.

FIG. 8 is a schematic sectional view of a three-way valve (Embodiment 2) of the present disclosure. FIG. 9 is a schematic perspective view of the three-way valve (Embodiment 2) of the present disclosure. FIGS. 8 and 9 show the second three-way valve 10B that is a three-way valve 10 according to Embodiment 2 of the present disclosure. As shown in FIGS. 8 and 9, in the second three-way valve 10B, the manifold 50 includes five plate-shaped manifold members 60, and the second three-way valve 10B is different from the first three-way valve 10A described above in this respect. In the following description, the manifold 50 in the second three-way valve 10B is also referred to as a second manifold 50B.

(Manifold of Three-Way Valve According to Embodiment 2)

Figure 10A:
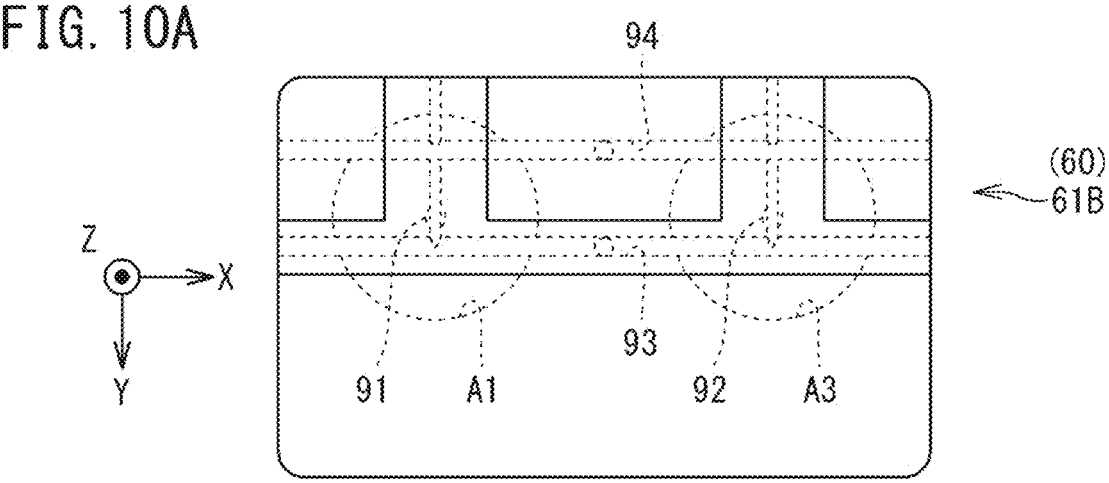
FIG. 10A is a top view of a first manifold member in a second three-way valve.
Figure 10B:
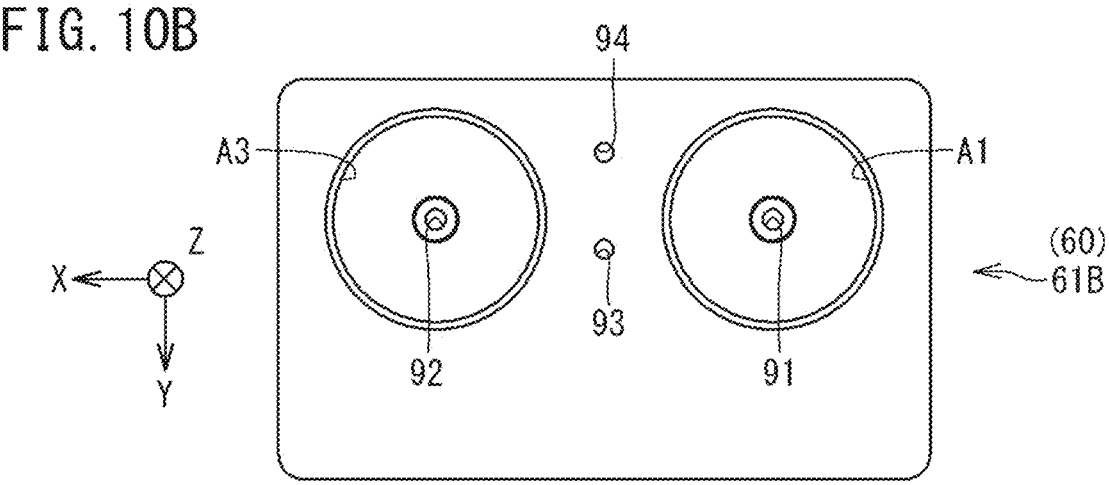
FIG. 10B is a bottom view of the first manifold member in the second three-way valve.
Figure 10C:
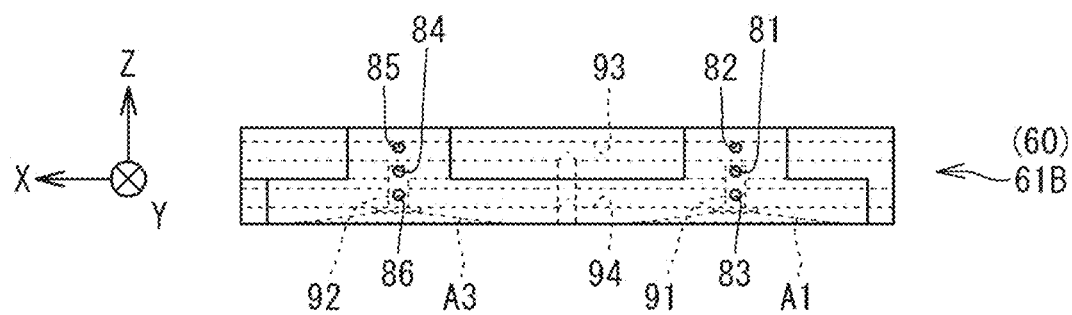
FIG. 10C is a rear view of the first manifold member in the second three-way valve.
Figure 11A:
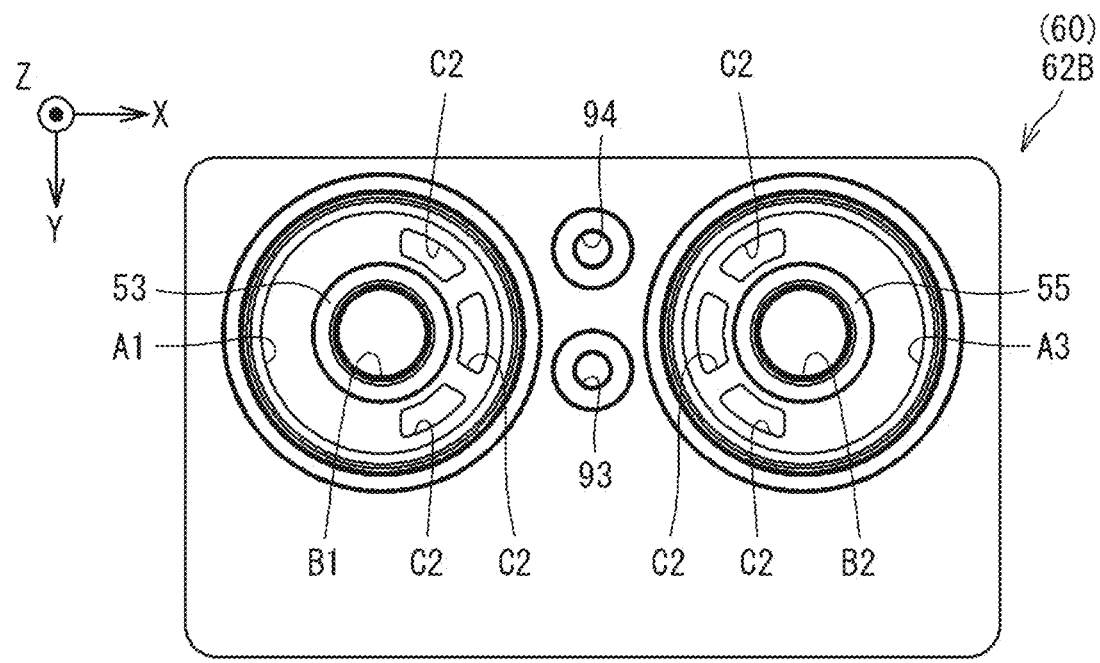
FIG. 11A is a top view of a second manifold member in the second three-way valve.
Figure 11B:
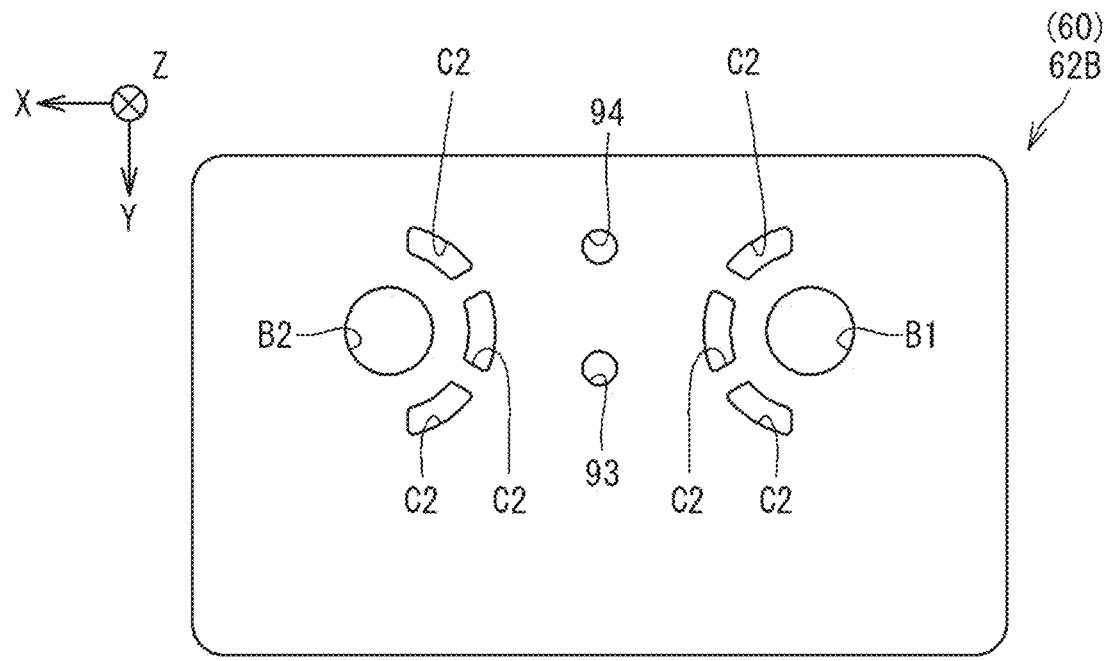
FIG. 11B is a bottom view of the second manifold member in the second three-way valve.
Figure 12A:
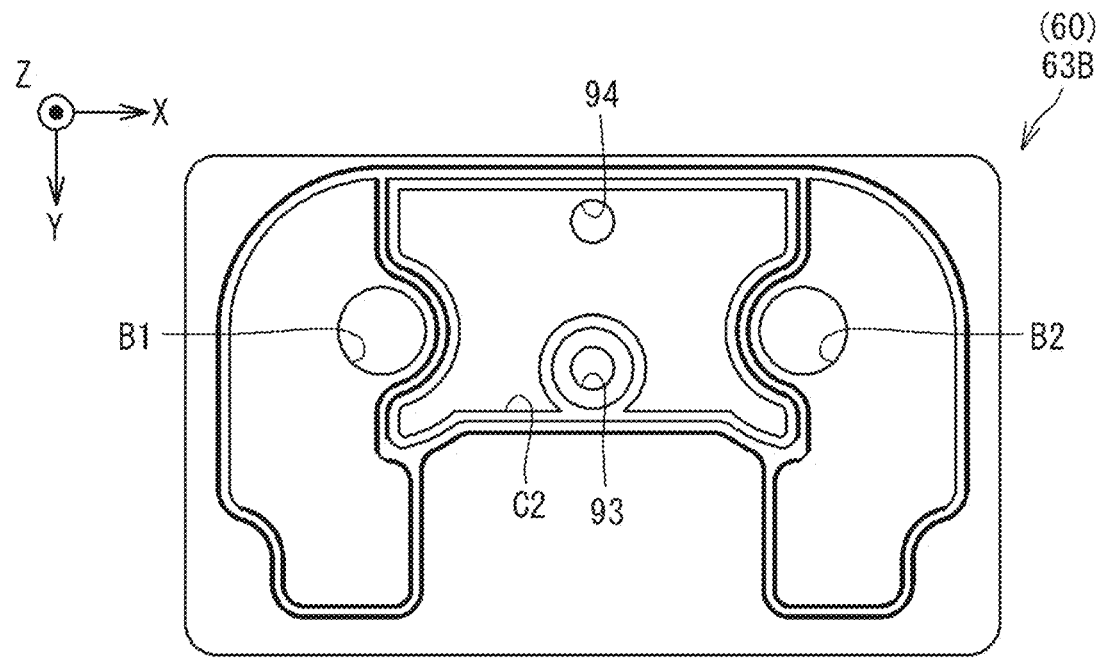
FIG. 12A is a top view of a third manifold member in the second three-way valve.
Figure 12B:
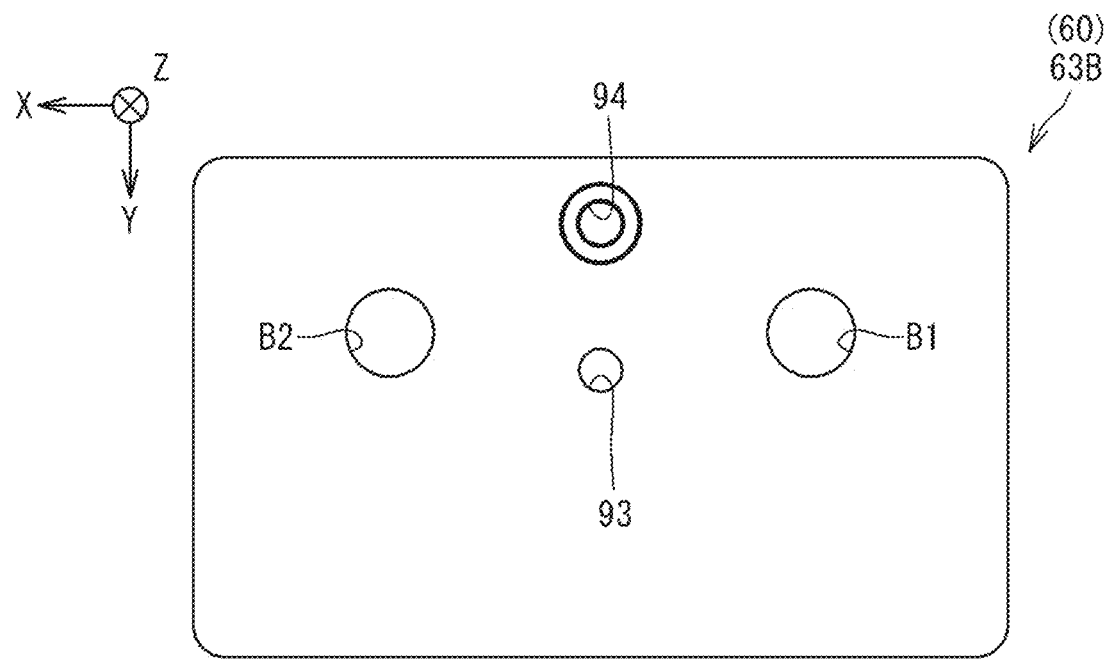
FIG. 12B is a bottom view of the third manifold member in the second three-way valve.
Figure 13A:
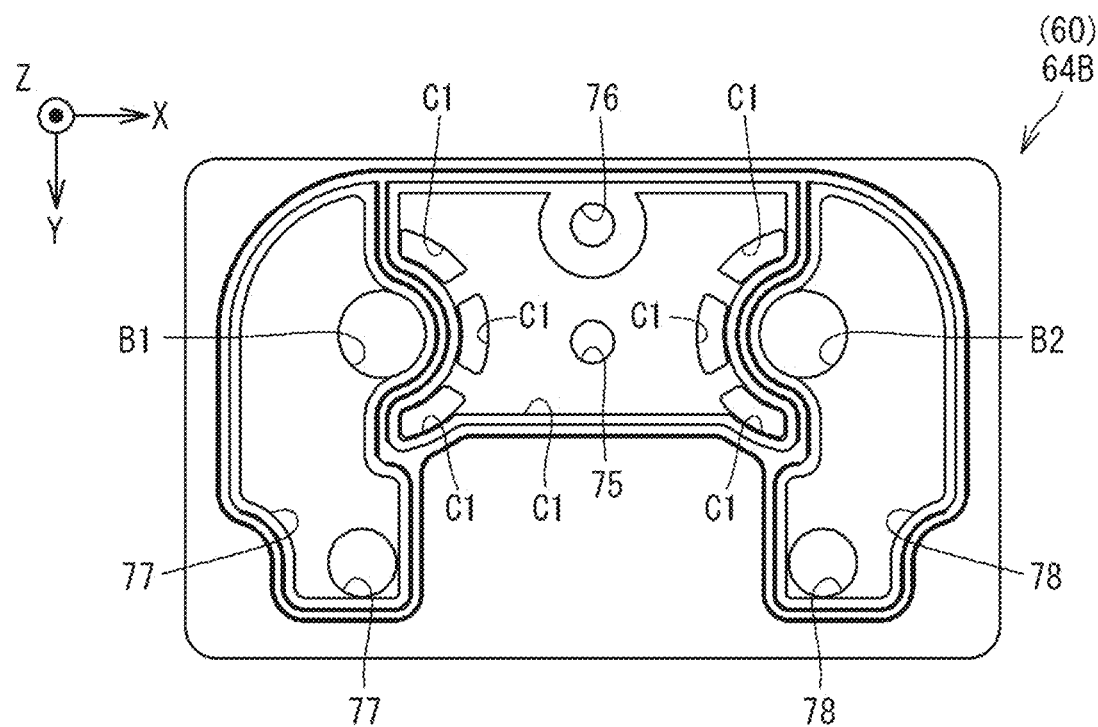
FIG. 13A is a top view of a fourth manifold member in the second three-way valve.
Figure 13B:
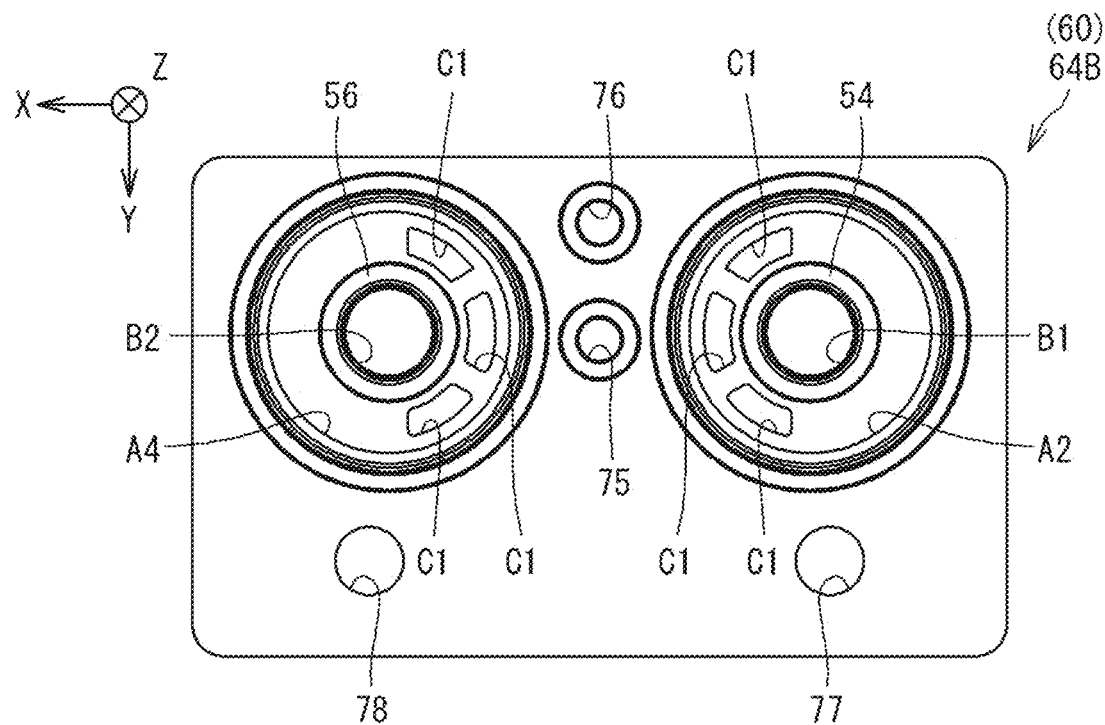
FIG. 13B is a bottom view of the fourth manifold member in the second three-way valve.
Figure 14A:
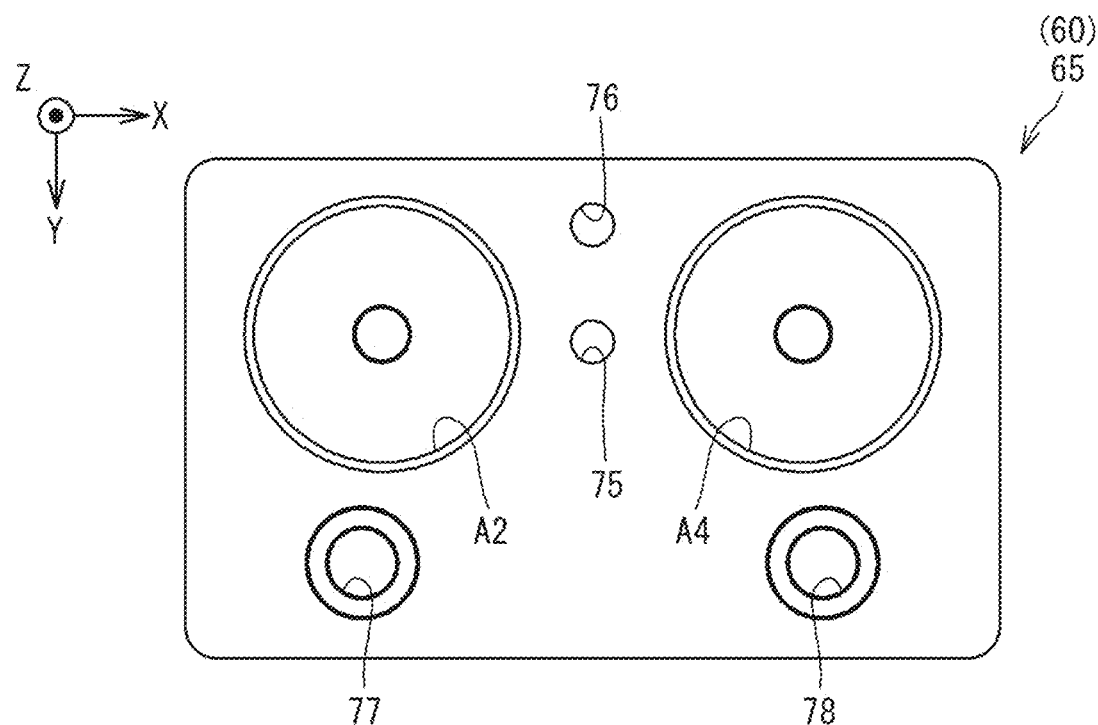
FIG. 14A is a top view of a fifth manifold member in the second three-way valve.
Figure 14B:
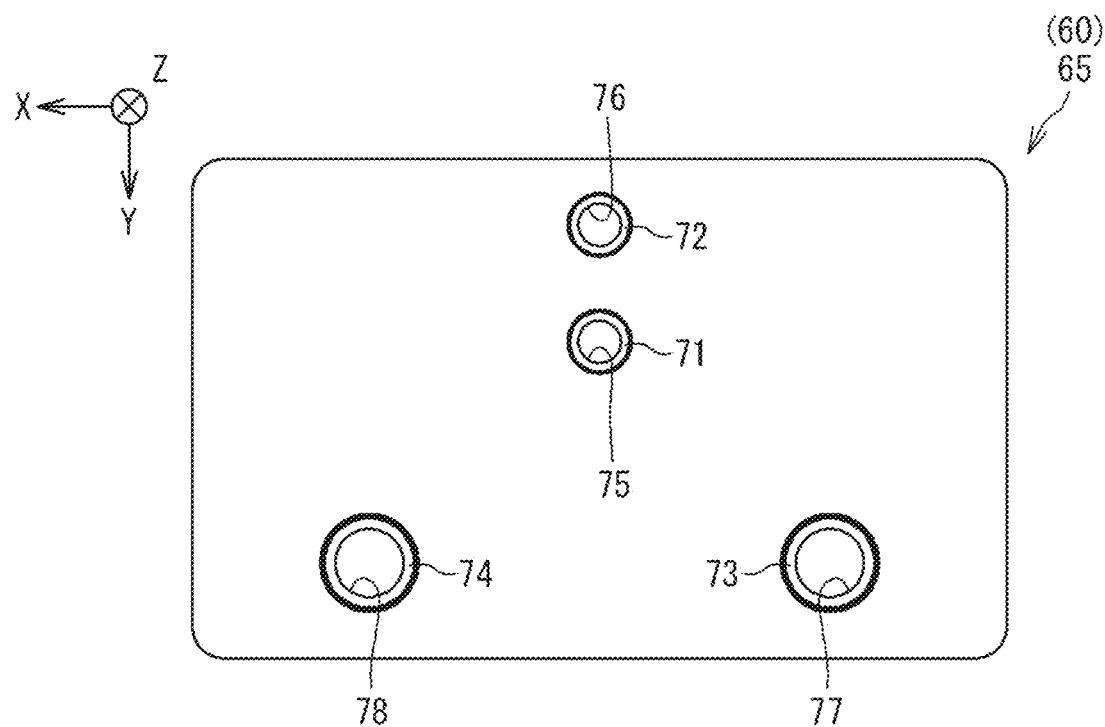
FIG. 14B is a bottom view of the fifth manifold member in the second three-way valve.

FIG. 10A is a top view of a first manifold member in the second three-way valve. FIG. 10B is a bottom view of the first manifold member in the second three-way valve. FIG. 10C is a rear view of the first manifold member in the second three-way valve. FIG. 11A is a top view of a second manifold member in the second three-way valve. FIG. 11B is a bottom view of the second manifold member in the second three-way valve. FIG. 12A is a top view of a third manifold member in the second three-way valve. FIG. 12B is a bottom view of the third manifold member in the second three-way valve. FIG. 13A is a top view of a fourth manifold member in the second three-way valve. FIG. 13B is a bottom view of the fourth manifold member in the second three-way valve. FIG. 14A is a top view of a fifth manifold member in the second three-way valve. FIG. 14B is a bottom view of the fifth manifold member in the second three-way valve. As shown in FIGS. 8 and 9, the second manifold 50B includes a first manifold member 60 (hereinafter, referred to as a first manifold member 61B), a second manifold member 60 (hereinafter, referred to as a second manifold member 62B), a third manifold member 60 (hereinafter, referred to as a third manifold member 63B), a fourth manifold member 60 (hereinafter, referred to as a fourth manifold member 64B), and a fifth manifold member 60 (hereinafter, referred to as a fifth manifold member 65).

The second manifold 50B is configured by stacking the first manifold member 61B, the second manifold member 62B, the third manifold member 63B, the fourth manifold member 64B, and the fifth manifold member 65 in the plate thickness direction in order from the upper side in the axial direction (Z direction) of the first coupling rod 23a accommodated in the first valve chamber 51 and the second coupling rod 24a accommodated in the second valve chamber 52.

As shown in FIGS. 8, 10A, and 10B, the first manifold member 61B is provided with a part of the first chamber A1, a part of the third chamber A3, the first pilot port 81, the second pilot port 82, the third pilot port 83, the fourth pilot port 84, the fifth pilot port 85, the sixth pilot port 86, the first pilot passage 91, the second pilot passage 92, a part of the third pilot passage 93, and a part of the fourth pilot passage 94.

As shown in FIGS. 8, 11A, and 11B, the second manifold member 62B is provided with a part of the first chamber A1, a part of the third chamber A3, a part of the first communication hole B1, a part of the second communication hole B2, a part of the second connecting passage C2, the first valve seat 53, the third valve seat 55, a part of the third pilot passage 93, and a part of the fourth pilot passage 94.

In the second manifold 50B, the first chamber A1 and the third chamber A3 are formed across the two manifold members 60, and are include first manifold member 61B and the second manifold member 62B.

As shown in FIGS. 8, 12A, and 12B, the third manifold member 63B is provided with a part of the first communication hole B1, a part of the second communication hole B2, a part of the first connecting passage C1, a part of the second connecting passage C2, a part of the exhaust passage 76, a part of the first air supply/exhaust passage 77, a part of the second air supply/exhaust passage 78, a part of the third pilot passage 93, and a part of the fourth pilot passage 94.

In the second manifold 50B, the second connecting passage C2 is configured by a recess formed in a range including a boundary surface between the second manifold member 62B and the third manifold member 63B. Specifically, the second connecting passage C2 is configured by a space surrounded by a lower surface (plane) of the second manifold member 62B and a recess formed on an upper surface of the third manifold member 63B. The second connecting passage C2 may be configured by a space surrounded by a recess formed in the lower surface of the second manifold member 62B and the upper surface (plane) of the third manifold member 63B, or may be configured by a space surrounded by a recess formed in the lower surface of the second manifold member 62B and the recess formed in the upper surface of the third manifold member 63B.

In other words, in the second manifold 50B, the second connecting passage C2 is formed in a range including the boundary surface between the adjacent manifold members 60 (the second manifold member 62B and the third manifold member 63B).

As shown in FIGS. 8, 13 A, and B, the fourth manifold member 64B is provided with a part of the second chamber A2, a part of the fourth chamber A4, a part of the first communication hole B1, a part of the second communication hole B2, a part of the first connecting passage C1, the second valve seat 54, the fourth valve seat 56, a part of the air supply passage 75, a part of the exhaust passage 76, a part of the first air supply/exhaust passage 77, and a part of the second air supply/exhaust passage 78.

In the second manifold 50B, the first connecting passage C1 is configured by a recess formed in a range including a boundary surface between the third manifold member 63B and the fourth manifold member 64B. Specifically, the first connecting passage C1 is configured by a space surrounded by a lower surface (plane) of the third manifold member 63B and a recess formed on an upper surface of the fourth manifold member 64B. The first connecting passage C1 may be configured by a space surrounded by the recess formed in the lower surface of the third manifold member 63B and the upper surface (plane) of the fourth manifold member 64B, or may be configured by a space surrounded by the recess formed in the lower surface of the third manifold member 63B and the recess formed in the upper surface of the fourth manifold member 64B.

In other words, in the second manifold 50B, the first connecting passage C1 is formed in a range including the boundary surface between the adjacent manifold members 60 (the third manifold member 63B and the fourth manifold member 64B). In the present embodiment, a case where both the first connecting passage C1 and the second connecting passage C2 are formed in the range including the boundary surface between the adjacent manifold members 60 is exemplified. However, the second manifold 50B of the present disclosure may have a configuration in which one of the first connecting passage C1 or the second connecting passage C2 is drilled in the manifold member 60.

As shown in FIGS. 8, 14A, and 14B, the fifth manifold member 65 is provided with a part of the second chamber A2, a part of the fourth chamber A4, the air supply port 71, a part of the air supply passage 75, the exhaust port 72, a part of the exhaust passage 76, the first air supply/exhaust port 73, a part of the first air supply/exhaust passage 77, the second air supply/exhaust port 74, and a part of the second air supply/exhaust passage 78.

In the second manifold 50B, the second chamber A2 and the fourth chamber A4 are formed across the two manifold members 60, and include the fourth manifold member 64B and the fifth manifold member 65.

In the second manifold 50B, the first communication hole B1 and the second communication hole B2 are formed to have axial directions parallel to the stacking direction of the manifold members 60. In the second manifold 50B, the first communication hole B1 and the second communication hole B2 are formed across three manifold members 60 (the second manifold member 62B, the third manifold member 63B, and the fourth manifold member 64B).

For example, in a case where two systems of passages (the first connecting passage C1 and the second connecting passage C2) extending in a direction orthogonal to the stacking direction are provided in one third manifold member 63A as in the first manifold 50A having a four-layer structure, there is a concern that expansion of each passage in the front-rear direction is restricted, and as a result, it becomes difficult to secure a cross-sectional area of each passage. On the other hand, in a case where one system of passage extending in a direction orthogonal to the stacking direction is provided in each of the third manifold member 63B and the fourth manifold member 64B as in the second manifold 50 having a five-layer structure, the restriction on expansion of each passage in the front-rear direction is relaxed, and as a result, the cross-sectional area of each passage (the first connecting passage C1 and the second connecting passage C2) is easily secured.

(Oxygen Concentrator of Present Disclosure)

Figure 15:
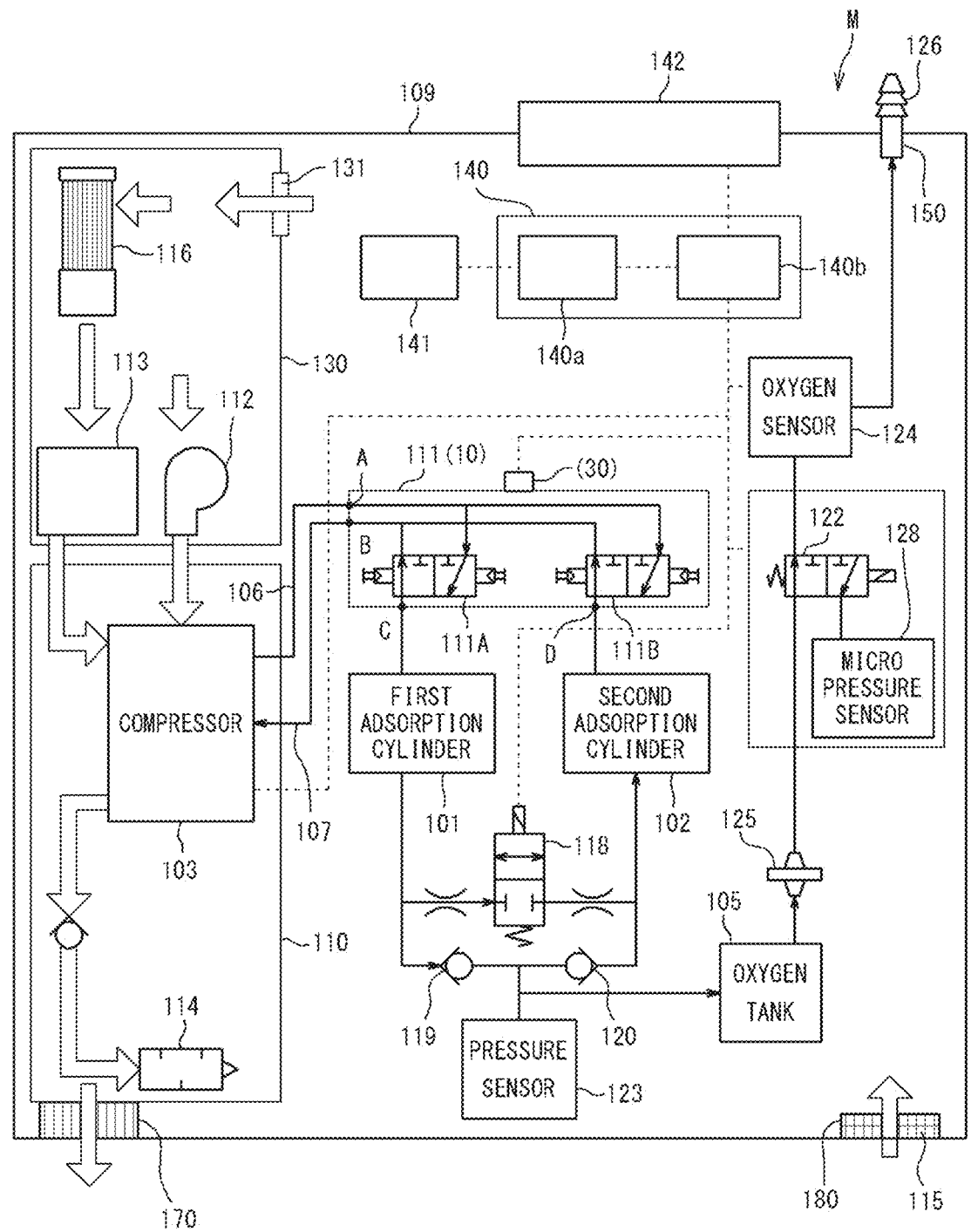
FIG. 15 is an explanatory diagram of an oxygen concentrator according to one embodiment of the present disclosure.
Figure 16:
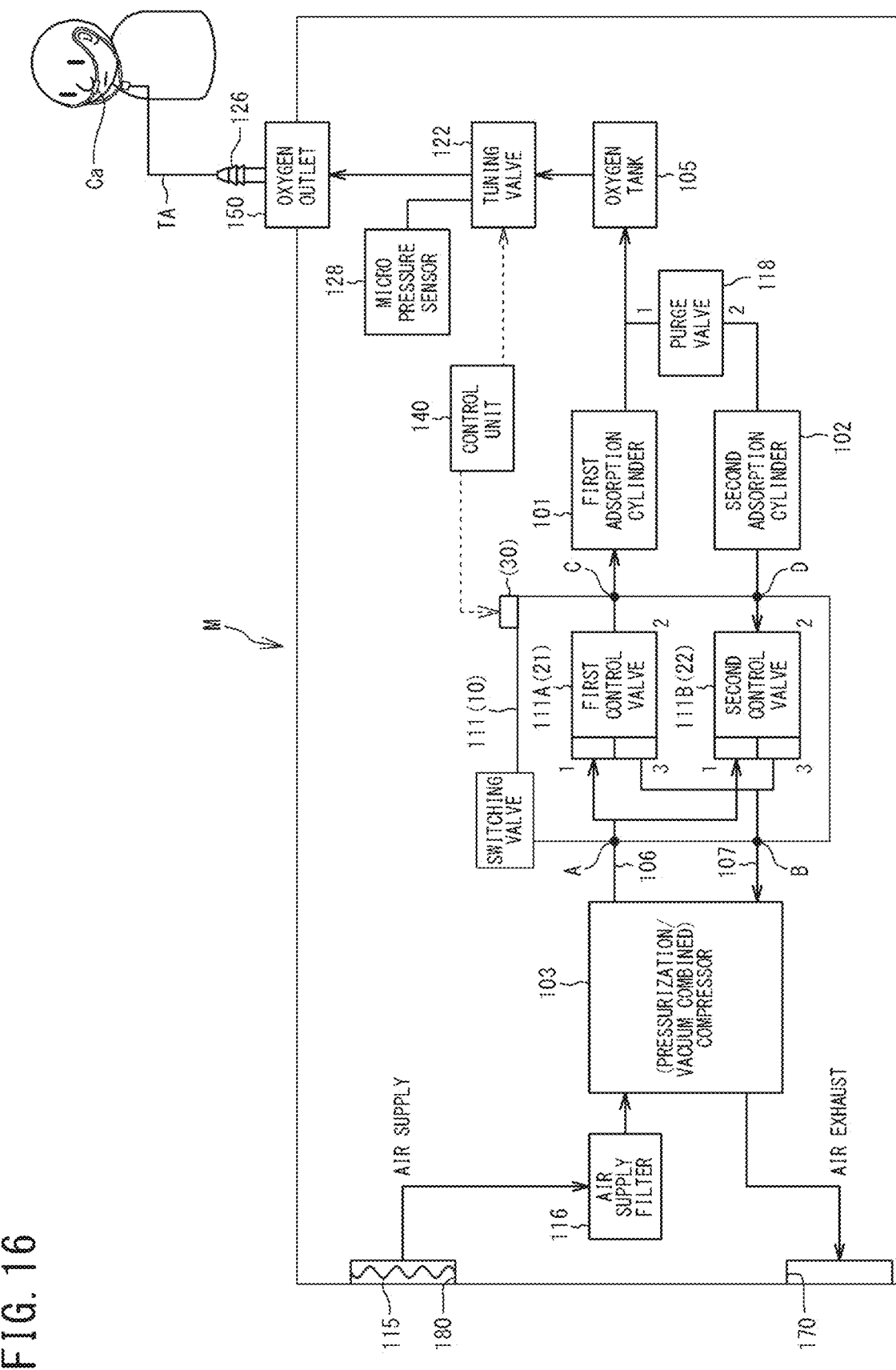
FIG. 16 is a block diagram for describing an oxygen concentration process of the oxygen concentrator.

FIG. 15 is an explanatory diagram of an oxygen concentrator according to one embodiment of the present disclosure. FIG. 16 is a block diagram for describing an oxygen concentration process of the oxygen concentrator. In FIG. 16, in order to facilitate understanding, some of the components or elements shown in FIG. 15 are simplified or omitted. An oxygen concentrator of the present disclosure is an apparatus that generates high concentration oxygen containing oxygen having an oxygen concentration higher than an oxygen concentration in air and supplies the high concentration oxygen to a user. The oxygen concentrator is used, for example, in home oxygen therapy for providing high concentration oxygen to a respiratory disease patient or the like who is a user.

(Configuration of Oxygen Concentrator M)

As shown in FIGS. 15 and 16, an oxygen concentrator M includes a first adsorption cylinder 101 and a second adsorption cylinder 102, a compressor 103 that supplies pressurized air to the first adsorption cylinder 101 and the second adsorption cylinder 102, and an oxygen tank 105 that stores high concentration oxygen. The compressor 103 according to the present embodiment is a pressurization/vacuum combined compressor capable of pressurizing and sucking gas such as air. The compressor 103 supplies pressurized air to the first adsorption cylinder 101 and the second adsorption cylinder 102, and desorbs and exhausts adsorbed nitrogen-rich gas by decompression. In the present embodiment, the pressurization/vacuum combined compressor 103 is used. However, the oxygen concentrator of the present disclosure may have a configuration in which a vacuum pump as an intake unit is separately provided in the apparatus, separately from the compressor that supplies the pressurized air.

The compressor 103 is activated and various electromagnetic valves and the like described later are activated by a control unit 140 disposed in the apparatus. The control unit 140 includes a storage unit 140a that stores a program for activating the oxygen concentrator M, and a calculation unit 140b that transmits an activation signal of an electromagnetic valve or the like. The control unit 140 is connected to a battery 141 serving as a power source in a state of not being connected to a power supply, and a display unit 142 that displays an activation state and the like of the oxygen concentrator M.

In the casing 109, a compressor box 110 accommodating the compressor 103 and an exhaust muffler 114, a cooling fan 112 for cooling the compressor 103, an air supply filter 116, and a fan box 130 accommodating an air supply silencing box 113 are provided. The compressor box 110, the air supply silencing box 113, and the fan box 130 constitute a silencing mechanism in the oxygen concentrator M. In other words, the compressor box 110, the air supply silencing box 113, and the fan box 130 can reduce noise generated by each device disposed in the casing 109.

In the casing 109, a switching valve 111 that switches a flow of the pressurized air from the compressor 103 to the first adsorption cylinder 101 and the second adsorption cylinder 102 and a flow of an exhaust gas from the first adsorption cylinder 101 and the second adsorption cylinder 102 to the compressor 103 is further provided. The switching valve 111 according to the present embodiment includes a first control valve 111A that is a three-port valve and a second control valve 111B that is also a three-port valve.

The oxygen concentrator M of the present disclosure employs the three-way valve 10 described above as the switching valve 111. The first control valve 111A corresponds to the first control valve 21 described above, and the second control valve 111B corresponds to the second control valve 22 described above. In FIG. 16, the numbers "1", "2", or "3" assigned to near the labels indicating the valves represent the port numbers of the valves. The three-port valves are assigned with numbers from "1" to "3", and two-port valves are assigned with number "1" and "2". The port "A" in the switching valve 111 in FIG. 15 corresponds to the air supply port 71, the port "B" corresponds to the exhaust port 72, the port "C" corresponds to the first air supply/exhaust port 73, and the port "D" corresponds to the second air supply/exhaust port 74.

The air supply port 180 provided in the casing 109 is provided with a dustproof filter 115 for collecting dust and the like contained in external air introduced into the apparatus. The external air introduced into the casing 109 through the dustproof filter 115 is sucked into the air supply filter 116 through the opening 131 of the fan box 130, passes through the air supply silencing box 113, and is sucked into the compressor 103. The air supply silencing box 113 is disposed in a flow path of air from the air supply filter 116 to the compressor 103, and reduces noise caused by air supply and compression of the compressor 103.

The air (pressurized air) compressed and pressurized by the compressor 103 is supplied to the first adsorption cylinder 101 and the second adsorption cylinder 102 via the first control valve 111A and the second control valve 111B. The exhaust gas from the first adsorption cylinder 101 and the second adsorption cylinder 102 is decompressed and sucked by the compressor 103 via the first control valve 111A and the second control valve 111B, and is exhausted from the exhaust muffler 114 to the outside from an exhaust port 170 via an opening 117 of the compressor box 110. The heat of the compressor 103 generated by the operation is sucked into the fan box 130 by the cooling fan 112 via the air supply port 180 of the casing 109 and the opening 131 of the fan box 130, and is cooled by air blown to the compressor 103 by the cooling fan 112.

An adsorbent that selectively or preferentially adsorbs nitrogen in the pressurized air supplied from the compressor 103 is accommodated inside the first adsorption cylinder 101 and the second adsorption cylinder 102. As the adsorbent, for example, zeolite or the like can be used. Details of the process of oxygen concentration using the first adsorption cylinder 101 and the second adsorption cylinder 102 will be described later.

Various valves for controlling a flow rate or a flow of a fluid such as high concentration oxygen, that is, a purge valve 118, check valves 119 and 120, and a tuning valve 122 are provided in a flow path (a flow path on an outlet side of high concentration oxygen, and in FIG. 15, a flow path from lower portions of the first adsorption cylinder 101 and the second adsorption cylinder 102 to a first oxygen outlet 150) downstream of the first adsorption cylinder 101 and the second adsorption cylinder 102. A micro pressure sensor 128 for detecting respiration of the user is attached to the tuning valve 122. The tuning valve 122 is switched to an "open" state or a "closed" state in accordance with a detection result of the micro pressure sensor 128. The oxygen tank 105 is provided upstream of the tuning valve 122 and downstream of the check valves 119 and 120. A pressure sensor 123 for detecting a pressure abnormality or the like is provided in a gas flow path between the check valves 119 and 120 and the oxygen tank 105.

The oxygen concentrator M according to the present embodiment is of an oxygen concentrator of the vacuum pressure swing adsorption system (VPSA) in which while air compressed by the compressor 103 is supplied to one adsorption cylinder, the other adsorption cylinder is sucked by the compressor 103 to be decompressed. However, the oxygen concentrator of the present disclosure is not limited to this apparatus, and may be an oxygen concentrator of the pressure swing adsorption system (PSA) in which while air compressed by a compressor is supplied to one adsorption cylinder, the other adsorption cylinder is opened to the atmosphere to be decompressed.

Each of the first control valve 111A and the second control valve 111B is a three-port valve, and switches between a pressurized state in which the pressurized air discharged from the compressor 103 is supplied to the first adsorption cylinder 101 (second adsorption cylinder 102) and a decompressed state in which the exhaust gas in the first adsorption cylinder 101 (second adsorption cylinder 102) is exhausted to the outside by suction. When one of the adsorption cylinders is in the pressurized state, the other adsorption cylinder is in the decompressed state.

The check valve 119 is disposed in a gas flow path downstream of the first adsorption cylinder 101, and the check valve 120 is disposed in a gas flow path downstream of the second adsorption cylinder 102. The check valves 119 and 120 are configured such that the high concentration oxygen exhausted from the first adsorption cylinder 101 and the second adsorption cylinder 102 flows only toward downstream. The purge valve 118 is disposed in a gas flow path connecting a gas flow path between the first adsorption cylinder 101 and the check valve 119 and a gas flow path between the second adsorption cylinder 102 and the check valve 120.

The high concentration oxygen from the check valve 119 and the high concentration oxygen from the check valve 120 are alternately supplied to the oxygen tank 105 and stored in the oxygen tank 105. A bacterial filter 125 for removing foreign substances from the high concentration oxygen and a tuning valve 122 for adjusting the flow rate of the high concentration oxygen from the oxygen tank 105 are disposed downstream of the oxygen tank 105. The high concentration oxygen having the flow rate adjusted by the tuning valve 122 is sent to the oxygen outlet 150 of the casing 109 via an oxygen sensor 124 for detecting an oxygen concentration abnormality. In the oxygen concentrator M, a cannula joint 126 is provided at the oxygen outlet 150, and the high concentration oxygen is supplied to a patient via a tube TA and a cannula Ca (see FIG. 16) connected to the cannula joint 126.

(Oxygen Concentration Process)

FIG. 17 is a diagram for describing a relationship between a pressure change of one cycle of an adsorption cylinder and a switching state of a control valve of the oxygen concentrator. Here, a process of generating high concentration oxygen in the oxygen concentrator M will be described.

In FIG. 17, the upper diagram shows an open/close state of the first control valve 111A, the second control valve 111B, and the purge valve 118 (see FIG. 16) in each step in relation to the oxygen concentration process, and the lower diagram shows a pressure change in the first adsorption cylinder 101 and the second adsorption cylinder 102 (see FIG. 16). In the lower diagram, a thick solid line indicates a pressure change inside the first adsorption cylinder 101, and a thin solid line indicates a pressure change inside the second adsorption cylinder 102. In the example shown in FIG. 17, a pressurization process in the adsorption cylinder is performed in the order of the first adsorption cylinder 101 and the second adsorption cylinder 102. In FIG. 17, one cycle of processing of the first adsorption cylinder 101 is performed in a period indicated by "T". The processing of one cycle includes six steps from "T1" to "T6" shown in the upper diagram.

In FIG. 16, the number assigned to each block indicating the first control valve 111A, the second control valve 111B, and the purge valve 118 represents the port number of each valve as described above. The first control valve 111A and the second control valve 111B, which are three-port valves, are assigned with three numbers from 1 to 3. The purge valve 118, which is a two-port valve, is assigned with two numbers from 1 to 2. In the upper diagram of FIG. 17, for example, "1 to 2" of the first control valve 111A being "open" indicates that a port indicated by "1" to a port indicated by "2" in the first control valve 111A are in a communicating state. At this time, in the first control valve 111A, a port indicated by "2" to a port indicated by "3" are in a non-communicating state.

In the lower diagram of FIG. 17, the horizontal axis indicates a lapse of time, and in the diagram, time passes from the left side to the right side. In step T1, the purge valve 118 is in the "open" state, and the high-concentration oxygen gas in the second adsorption cylinder 102 is supplied from the second adsorption cylinder 102 to the first adsorption cylinder 101. In step T1, since the ports "2" to "3" of the first control valve 111A and the second control valve 111B are both in the "closed" state, the insides of the first adsorption cylinder 101 and the second adsorption cylinder 102 are not sucked. The suction of the first adsorption cylinder 101 and the suction of the second adsorption cylinder 102 are performed such that the timing is deviated from each other by controlling the opening and closing of the valve.

In subsequent step T2, the ports "1" to "2" of the first control valve 111A and the ports "2" to "3" of the second control valve 111B are in the "open" state, and pressurization of the first adsorption cylinder 101 and decompression of the second adsorption cylinder 102 by the compressor 103 are performed. In step T2, the purge valve 118 in the "open" state in step T1 is in the "closed" state. In the first adsorption cylinder 101 in the pressurized state by the supply of the pressurized air, nitrogen contained in the pressurized air is adsorbed by the adsorbent accommodated in the first adsorption cylinder 101. As a result, the gas in the first adsorption cylinder 101 becomes high concentration oxygen having a higher oxygen concentration than a normal oxygen concentration in the air.

In subsequent step T3, the purge valve 118 is in the "open" state, and the high concentration oxygen in the first adsorption cylinder 101 is supplied into the second adsorption cylinder 102 via the purge valve 118.

In subsequent step T4, the ports "2" to "3" of the first control valve 111A and the ports "2" to "3" of the second control valve 111B are in the "closed" state. In step T4, the supply of high concentration oxygen from the first adsorption cylinder 101 to the second adsorption cylinder 102 in step T3 is continued.

In subsequent step T5, the ports "2" to "3" of the first control valve 111A and the ports "1" to "2" of the second control valve 111B are in the "open" state, and pressurization of the second adsorption cylinder 102 and decompression of the first adsorption cylinder 101 by the compressor 103 are performed. In step T4, the purge valve 118 in the "open" state in step T3 is in the "closed" state. In the second adsorption cylinder 102 in the pressurized state by the supply of the pressurized air, nitrogen contained in the pressurized air is adsorbed by the adsorbent accommodated in the second adsorption cylinder 102. As a result, the gas in the second adsorption cylinder 102 becomes high concentration oxygen having a higher oxygen concentration than the normal oxygen concentration in the air.

In subsequent step T6, the purge valve 118 is in the "open" state, and the high concentration oxygen in the second adsorption cylinder 102 is supplied into the first adsorption cylinder 101 via the purge valve 118. Thereafter, steps T1 to T6 described above are repeated. The oxygen concentrator M generates high concentration oxygen by repeating steps T1 to T6 in the first adsorption cylinder 101 and the second adsorption cylinder 102, and stores the generated high concentration oxygen in the oxygen tank 105.

Functional Effects of Embodiments (1)

The three-way valve 10 according to the above embodiment includes the manifold 50 provided with a flow path including the air supply port 71, the air supply passage 75 leading to the air supply port 71, the exhaust port 72, the exhaust passage 76 leading to the exhaust port 72, the air supply/exhaust ports 73 and 74, the air supply/exhaust passages 77 and 78 leading to the air supply/exhaust ports 73 and 74, and the valve chambers 51 and 52 that communicate with the air supply passage 75, the exhaust passage 76 and the air supply/exhaust passages 77 and 78, the valve bodies 23 and 24 that are accommodated in the valve chambers 51 and 52 and are displaceable to the first position at which the air supply port 71 communicates with the air supply/exhaust passages 77 and 78 or the second position at which the exhaust port 72 communicates with the air supply/exhaust passages 77 and 78, and the pilot mechanism 30 that switches the positions of the valve bodies 23 and 24 to the first position or the second position. In the three-way valve 10, the manifold 50 is configured by the plurality of manifold members 60 that has a plate shape and is stacked in the plate thickness direction.

In this three-way valve 10, by adopting the manifold 50 having a stacked structure, the sectional shape of the passage constituting each flow path in the manifold 50 can be a shape other than circular, and a space efficiency in the manifold 50 (a ratio of a space to be secured in the manifold 50 to a volume of the manifold 50) can be increased. As a result, the three-way valve 10 can be reduced in size and weight.

(2)

In the three-way valve 10 according to the above embodiment, the flow path provided in the manifold 50 includes the first valve chamber 51, the second valve chamber 52, the first connecting passage C1 that allows the first valve chamber 51 and the second valve chamber 52 to communicate with each other and is connected to the air supply passage 75, the second connecting passage C2 that allows the first valve chamber 51 and the second valve chamber 52 to communicate with each other and is connected to the exhaust passage 76, the first air supply/exhaust port 73 on a side of the first valve chamber 51, the first air supply/exhaust passage 77 on a side of the first valve chamber 51, the second air supply/exhaust port 74 on a side of the second valve chamber 52, and the second air supply/exhaust passage 78 on a side of the second valve chamber 52. In the three-way valve 10, the valve body includes the first valve body 23 and the second valve body 24, the first valve body 23 is accommodated in the first valve chamber 51, and the second valve body 24 is accommodated in the second valve chamber 52.

The three-way valve 10 can be reduced in size and weight in a case of being a double three-way valve.

(3)

In the three-way valve 10 according to the above embodiment, the first connecting passage C1 and the second connecting passage C2 are constituted by the recess in the boundary surface between the adjacent manifold members 60 of the plurality of manifold members.

The three-way valve 10 with the manifold 50 in a stacked structure enables the first connecting passage C1 and the second connecting passage C2 to be formed at a boundary portion of the manifold member 60. As a result, the space efficiency in the manifold 50 can be increased, and the manifold 50 can be downsized.

(4)

In the three-way valve 10 according to the above embodiment, the flow path provided in the manifold 50 further includes the first pilot passage 91 that communicates the air supply passage 75 or the exhaust passage 76 with the first valve chamber 51, and the second pilot passage 92 that communicates the air supply passage 75 or the exhaust passage 76 with the second valve chamber 52. The first valve body 23 includes the first diaphragm 23b and the second diaphragm 23c that are deformable by the pressure of the fluid supplied to the first valve chamber 51 via the first pilot passage 91. The second valve body 24 includes the third diaphragm 24b and the fourth diaphragm 24c that are deformable by the pressure of the fluid supplied to the second valve chamber 52 via the second pilot passage 92. The pilot mechanism 30 includes the first pilot valve 31 and the second pilot valve 32. In the pilot mechanism 30, the first pilot valve 31 and the second pilot valve 32 switch a supply destination of the fluid to one of the first pilot passage 91 or the second pilot passage 92, and the first diaphragm 23b and the second diaphragm 23c are deformed or the third diaphragm 24b and the fourth diaphragm 24c are deformed to position one of the first valve body 23 or the second valve body 24 at the first position P1 and another one of the first valve body 23 or the second valve body 24 at the second position P2.

The three-way valve 10 can be reduced in size and weight in a case of being a pilot type three-way valve activated by a pilot pressure.

(5)

In the three-way valve 10 according to the above embodiment, the flow path provided in the manifold 50 further includes the fourth pilot passage 94 that allows the first pilot passage 91 or the second pilot passage 92 and the exhaust passage 76 to communicate with each other. In the three-way valve 10, the first pilot valve 31 and the second pilot valve 32 switch a communication destination of the fourth pilot passage 94 to one of the first pilot passage 91 or the second pilot passage 92 to deform the first diaphragm 23b or the third diaphragm 24b.

In the three-way valve 10, in a case where air is sucked and exhausted from the exhaust port 72, it is possible to increase reliability of displacement operations of the first valve body 23 and the second valve body 24.

(6)

In the three-way valve 10 according to the above embodiment, the first valve body 23 includes the first coupling rod 23a, the first diaphragm 23b coupled to one end of the first coupling rod 23a, the second diaphragm 23c coupled to the other end of the first coupling rod 23a, the first valve portion 23d provided closer to the first diaphragm 23b of the first coupling rod 23a, and the second valve portion 23e provided closer to the second diaphragm 23c of the first coupling rod 23a. The second valve body 24 includes the second coupling rod 24a, the third diaphragm 24b coupled to one end of the second coupling rod 24a, the fourth diaphragm 24c coupled to another end of the second coupling rod 24a, the third valve portion 24d provided closer to the third diaphragm 24b of the second coupling rod 24a, and the fourth valve portion 24e provided closer to the fourth diaphragm 24c of the second coupling rod 24a. The first valve chamber 51 includes the first chamber A1 that accommodates the first diaphragm 23b, the second chamber A2 that accommodates the second diaphragm 23c, the first communication hole B1 that allows the first chamber A1 and the second chamber A2 to communicate with each other and accommodates the first coupling rod 23a, the first valve seat 53 formed at an end of the first communication hole B1 closer to the first chamber A1 and facing the first valve portion 23d, and the second valve seat 54 formed at an end of the first communication hole B1 closer to the second chamber A2 and facing the second valve portion 23e. The second valve chamber 52 includes the third chamber A3 that accommodates the third diaphragm 24b, the fourth chamber A4 that accommodates the fourth diaphragm 24c, the second communication hole B2 that allows the third chamber A3 and the fourth chamber A4 to communicate with each other and accommodates the second coupling rod 24a, the third valve seat 55 formed at an end of the second communication hole B2 closer to the third chamber A3 and facing the third valve portion 24d, and the fourth valve seat 56 formed at an end of the second communication hole B2 closer to the fourth chamber A4 and facing the fourth valve portion 24e. The first connecting passage C1 allows the second chamber A2 and the fourth chamber A4 to communicate with each other, the second connecting passage C2 allows the first chamber A1 and the third chamber A3 to communicate with each other, the third pilot passage 93 communicates with the air supply passage 75 via the first access passage C1, and the fourth pilot passage 94 communicates with the exhaust passage 76 via the second access passage C2.

The three-way valve 10 can be reduced in size and weight in a case of being an internal pilot type double three-way valve.

(7)

In the three-way valve 10 according to the above embodiment, in the manifold 50, the first communication hole B1 and the second communication hole B2 has an axial direction that is parallel to the stacking direction (Z direction) of the plurality of manifold members 60. In the manifold 50, the first chamber A1, the second chamber A2, the third chamber A3, the fourth chamber A4, the first communication hole B1, and the second communication hole B2 are formed across two or more manifold members 60.

In the three-way valve 10, the internal pilot type double three-way valve can be configured by using the manifold 50 having a stacked structure. As a result, the internal pilot type double three-way valve can be reduced in size and weight.

(8)

The oxygen concentrator M according to the above embodiment generates high concentration oxygen containing oxygen having a higher concentration than the oxygen concentration in the air and supplies the generated high concentration oxygen. The oxygen concentrator M includes an adsorbent that allows adsorption of nitrogen or oxygen contained in the air and desorption of the nitrogen or oxygen adsorbed, the first adsorption cylinder 101 and the second adsorption cylinder 102 that accommodate the adsorbent, the air supply pipe 106 that supplies the air as a raw material of the high concentration oxygen to the first adsorption cylinder 101 and the second adsorption cylinder 102, the exhaust pipe 107 that exhausts, from the first adsorption cylinder 101 and the second adsorption cylinder 102, the high concentration oxygen generated, and the switching valve 111 that alternately selects the first adsorption cylinder 101 or the second adsorption cylinder 102, and connects one of the first adsorption cylinder 101 or the second adsorption cylinder 102 selected to the air supply pipe 106, while connecting another one of the first adsorption cylinder 101 or the second adsorption cylinder 102 to the exhaust pipe 107, in which the switching valve 111 includes the three-way valve 10.

The oxygen concentrator M, which employs the three-way valve 10 as the switching valve 111, can be reduced in size and weight. As the oxygen concentrator M, there are a portable type suitable for outdoor use and a stationary type suitable for indoor use. In the oxygen concentrator M, it is preferable to employ the three-way valve 10 as the switching valve 111 regardless of the portable type or the stationary type, but in the case of the portable type, it is particularly preferable to employ the three-way valve 10 as the switching valve 111.

Although the oxygen concentration apparatus of the present disclosure uses a nitrogen adsorbent such as zeolite as an adsorbent, the present disclosure may be applied to an oxygen concentrator using an oxygen adsorbent as an adsorbent.

The invention claimed is:

1. A three-way valve comprising:
   a manifold provided with a flow path including a first port, a first passage leading to the first port, a second port, a second passage leading to the second port, a third port, a third passage leading to the third port, and a valve chamber that communicates with the first passage, the second passage, and the third passage;
   a valve body that is accommodated in the valve chamber and is displaceable to
      a first position at which the first port and the third port communicate with each other or
      a second position at which the second port and the third port communicate with each other; and
   a switching mechanism configured to switch a position of the valve body to the first position or the second position,
   the manifold being configured by a plurality of manifold members that have a plate shape and are stacked in a plate thickness direction.

2. The three-way valve according to claim 1, wherein the flow path provided in the manifold includes
   a first valve chamber as a first of the valve chamber,
   a second valve chamber as a second of the valve chamber,
   a first connecting passage that allows the first valve chamber and the second valve chamber to communicate with each other and is connected to the first passage,
   a second connecting passage that allows the first valve chamber and the second valve chamber to communicate with each other and is connected to the second passage,
   a first valve chamber side third port that is the third port on a side of the first valve chamber,
   a first valve chamber side third passage that is the third passage on a side of the first valve chamber,
   a second valve chamber side third port that is the third port on a side of the second valve chamber, and
   a second valve chamber side third passage that is the third passage on a side of the second valve chamber,
   the valve body includes a first valve body as a first of the valve body, and a second valve body as a second of the valve body, and
   the first valve body is accommodated in the first valve chamber, and the second valve body is accommodated in the second valve chamber.

3. The three-way valve according to claim 2, wherein at least one of the first connecting passage and the second connecting passage is formed by a recess in a boundary surface between adjacent manifold members of the plurality of manifold members.

4. The three-way valve according to claim 2, wherein the flow path provided in the manifold further includes a first pilot passage that communicates with the first valve chamber, a second pilot passage that communicates with the second valve chamber, and a third pilot passage that allows the first pilot passage or the second pilot passage and the first passage to communicate with each other, the first valve body further includes a first diaphragm and a second diaphragm that are deformable by a pressure of a fluid supplied to the first valve chamber via the first pilot passage, the second valve body further includes a third diaphragm and a fourth diaphragm that are deformable by the pressure of the fluid supplied to the second valve chamber via the second pilot passage, the switching mechanism includes a pilot valve that switches a communication destination of the third pilot passage to one of the first pilot passage or the second pilot passage, and the first diaphragm and the second diaphragm are deformed and the third diaphragm and the fourth diaphragm are deformed to position one of the first valve body or the second valve body at the first position and position another one of the first valve body or the second valve body at the second position.

5. The three-way valve according to claim 4, wherein the flow path provided in the manifold further includes a fourth pilot passage that allows the first pilot passage or the second pilot passage and the second passage to communicate with each other, and the pilot valve switches a communication destination of the fourth pilot passage to one of the first pilot passage or the second pilot passage to deform the first diaphragm and the second diaphragm or the third diaphragm and the fourth diaphragm.

6. The three-way valve according to claim 5, wherein the first valve body includes a first coupling rod, the first diaphragm coupled to one end of the first coupling rod, the second diaphragm coupled to another end of the first coupling rod, a first valve portion provided on the first diaphragm, and a second valve portion provided on the second diaphragm, the second valve body includes a second coupling rod, the third diaphragm coupled to one end of the second coupling rod, the fourth diaphragm coupled to another end of the second coupling rod, a third valve portion provided on the third diaphragm, and a fourth valve portion provided on the fourth diaphragm, the first valve chamber includes a first chamber that accommodates the first diaphragm, a second chamber that accommodates the second diaphragm, a first communication hole that allows the first chamber and the second chamber to communicate with each other and accommodates the first coupling rod, a first valve seat formed at an end of the first communication hole closer to the first chamber and facing the first valve portion, and a second valve seat formed at an end of the first communication hole closer to the second chamber and facing the second valve portion, the second valve chamber includes a third chamber that accommodates the third diaphragm, a fourth chamber that accommodates the fourth diaphragm, a second communication hole that allows the third chamber and the fourth chamber to communicate with each other and accommodates the second coupling rod, a third valve seat formed at an end of the second communication hole closer to the third chamber and facing the third valve portion, and a fourth valve seat formed at an end of the second communication hole closer to the fourth chamber and facing the fourth valve portion, the first connecting passage allows the second chamber and the fourth chamber to communicate with each other, the second connecting passage allows the first chamber and the third chamber to communicate with each other, the third pilot passage communicates with the first passage via the first connecting passage, and the fourth pilot passage communicates with the second passage via the second connecting passage.

7. The three-way valve according to claim 6, wherein in the manifold, each of the first communication hole and the second communication hole has an axial direction that is parallel to a stacking direction of the plurality of manifold members, and the first chamber, the second chamber, the third chamber, the fourth chamber, the first communication hole, and the second communication hole are formed across two or more manifold members of the plurality of manifold members.

8. An oxygen concentrator including the three-way valve according to claim 4, the oxygen concentrator generating high concentration oxygen containing oxygen at a concentration higher than an oxygen concentration in air and supplies the high concentration oxygen generated, the oxygen concentrator further comprising:

an adsorbent that allows adsorption of nitrogen or oxygen contained in the air and desorption of the nitrogen or oxygen adsorbed;

a first adsorption cylinder and a second adsorption cylinder that accommodate the adsorbent;

an air supply pipe that supplies the air as a raw material of the high concentration oxygen to the first adsorption cylinder and the second adsorption cylinder;

an exhaust pipe that exhausts, from the first adsorption cylinder and the second adsorption cylinder, the high concentration oxygen generated; and a switching valve that alternately selects the first adsorption cylinder or the second adsorption cylinder, and connects one of the first adsorption cylinder or the second adsorption cylinder selected to the air supply pipe while connecting another one of the first adsorption cylinder or the second adsorption cylinder to the exhaust pipe, the switching valve including the three-way valve.

9. The three-way valve according to claim 3, wherein the flow path provided in the manifold further includes a first pilot passage that communicates with the first valve chamber, a second pilot passage that communicates with the second valve chamber, and a third pilot passage that allows the first pilot passage or the second pilot passage and the first passage to communicate with each other, the first valve body further includes a first diaphragm and a second diaphragm that are deformable by a pressure of a fluid supplied to the first valve chamber via the first pilot passage, the second valve body further includes a third diaphragm and a fourth diaphragm that are deformable by the pressure of the fluid supplied to the second valve chamber via the second pilot passage, the switching mechanism includes a pilot valve that switches a communication destination of the third pilot passage to one of the first pilot passage or the second pilot passage, and the first diaphragm and the second diaphragm are deformed and the third diaphragm and the fourth diaphragm are deformed to position one of the first valve body or the second valve body at the first position and position another one of the first valve body or the second valve body at the second position.

10. The three-way valve according to claim 9, wherein the flow path provided in the manifold further includes a fourth pilot passage that allows the first pilot passage or the second pilot passage and the second passage to communicate with each other, and the pilot valve switches a communication destination of the fourth pilot passage to one of the first pilot passage or the second pilot passage to deform the first diaphragm and the second diaphragm or the third diaphragm and the fourth diaphragm.

11. The three-way valve according to claim 10, wherein the first valve body includes a first coupling rod, the first diaphragm coupled to one end of the first coupling rod, the second diaphragm coupled to another end of the first coupling rod, a first valve portion provided on the first diaphragm, and a second valve portion provided on the second diaphragm, the second valve body includes a second coupling rod, the third diaphragm coupled to one end of the second coupling rod, the fourth diaphragm coupled to another end of the second coupling rod, a third valve portion provided on the third diaphragm, and a fourth valve portion provided on the fourth diaphragm, the first valve chamber includes a first chamber that accommodates the first diaphragm, a second chamber that accommodates the second diaphragm, a first communication hole that allows the first chamber and the second chamber to communicate with each other and accommodates the first coupling rod, a first valve seat formed at an end of the first communication hole closer to the first chamber and facing the first valve portion, and a second valve seat formed at an end of the first communication hole closer to the second chamber and facing the second valve portion, the second valve chamber includes a third chamber that accommodates the third diaphragm, a fourth chamber that accommodates the fourth diaphragm, a second communication hole that allows the third chamber and the fourth chamber to communicate with each other and accommodates the second coupling rod, a third valve seat formed at an end of the second communication hole closer to the third chamber and facing the third valve portion, and a fourth valve seat formed at an end of the second communication hole closer to the fourth chamber and facing the fourth valve portion, the first connecting passage allows the second chamber and the fourth chamber to communicate with each other, the second connecting passage allows the first chamber and the third chamber to communicate with each other, the third pilot passage communicates with the first passage via the first connecting passage, and the fourth pilot passage communicates with the second passage via the second connecting passage.

12. The three-way valve according to claim 11, wherein in the manifold, each of the first communication hole and the second communication hole has an axial direction that is parallel to a stacking direction of the plurality of manifold members, and the first chamber, the second chamber, the third chamber, the fourth chamber, the first communication hole, and the second communication hole are formed across two or more manifold members of the plurality of manifold members.

13. An oxygen concentrator including the three-way valve according to claim 9, the oxygen concentrator generating high concentration oxygen containing oxygen at a concentration higher than an oxygen concentration in air and supplies the high concentration oxygen generated, the oxygen concentrator further comprising:

an adsorbent that allows adsorption of nitrogen or oxygen contained in the air and desorption of the nitrogen or oxygen adsorbed;

a first adsorption cylinder and a second adsorption cylinder that accommodate the adsorbent;

an air supply pipe that supplies the air as a raw material of the high concentration oxygen to the first adsorption cylinder and the second adsorption cylinder;

an exhaust pipe that exhausts, from the first adsorption cylinder and the second adsorption cylinder, the high concentration oxygen generated; and a switching valve that alternately selects the first adsorption cylinder or the second adsorption cylinder, and connects one of the first adsorption cylinder or the second adsorption cylinder selected to the air supply pipe while connecting another one of the first adsorption cylinder or the second adsorption cylinder to the exhaust pipe, the switching valve including the three-way valve.

* * * * *